(12) United States Patent
Komada et al.

(10) Patent No.: US 7,087,551 B2
(45) Date of Patent: Aug. 8, 2006

(54) CATALYST FOR USE IN CATALYTIC OXIDATION OR AMMOXIDATION OF PROPANE OR ISOBUTANE IN THE GASEOUS PHASE

(75) Inventors: Satoru Komada, Yokosuka (JP); Hidenori Hinago, Kurashiki (JP); Osamu Nagano, Yokohama (JP); Mamoru Watanabe, Okayama-ken (JP)

(73) Assignee: Asahi Kasei Kabushiki Kaisha, Osaka (JP)

( * ) Notice: Subject to any disclaimer, the term of this patent is extended or adjusted under 35 U.S.C. 154(b) by 343 days.

(21) Appl. No.: 10/231,113

(22) Filed: Aug. 30, 2002

(65) Prior Publication Data

US 2003/0088118 A1   May 8, 2003

Related U.S. Application Data

(63) Continuation-in-part of application No. PCT/JP01/05055, filed on Jun. 14, 2001.

(30) Foreign Application Priority Data

Jun. 15, 2000   (JP)   ............................. 2000-179687

(51) Int. Cl.
  *B01J 27/19*   (2006.01)
  *B01J 23/14*   (2006.01)
  *C07C 253/18*   (2006.01)

(52) U.S. Cl. ...................... 502/211; 502/321; 558/318; 558/319

(58) Field of Classification Search ................ 558/321, 558/318, 319; 502/215, 309, 211, 321
See application file for complete search history.

(56) References Cited

U.S. PATENT DOCUMENTS

| | | | |
|---|---|---|---|
| 4,871,706 A | 10/1989 | Brazdil, Jr. et al. | |
| 5,231,214 A | 7/1993 | Ushikubo et al. | |
| 5,281,745 A | 1/1994 | Ushikubo et al. | |
| 5,380,933 A | 1/1995 | Ushikubo et al. | |
| 5,472,925 A | 12/1995 | Ushikubo et al. | |
| 5,663,392 A | 9/1997 | Albonetti et al. | |
| 5,686,381 A | 11/1997 | Albonetti et al. | |
| 5,750,760 A | 5/1998 | Ushikubo et al. | |
| 6,036,880 A | 3/2000 | Komada et al. | |
| 6,043,185 A | 3/2000 | Cirjak et al. | |
| 6,043,186 A * | 3/2000 | Komada et al. | 502/312 |
| 6,143,690 A * | 11/2000 | Komada et al. | 502/211 |
| 6,156,920 A | 12/2000 | Brazdil, Jr. et al. | |
| 6,200,926 B1 | 3/2001 | Blanchard et al. | |

FOREIGN PATENT DOCUMENTS

| | | |
|---|---|---|
| EP | 0 608 838 B1 | 8/1994 |
| EP | 0 767 164 B1 | 4/1997 |
| EP | 0 945 432 A1 | 9/1999 |
| JP | 9-316023 A | 12/1997 |
| JP | 10-28862 A | 2/1998 |
| JP | 10-45664 A | 2/1998 |
| JP | 10-57813 A | 3/1998 |
| JP | 10-330343 A | 12/1998 |
| JP | 11-57479 A | 3/1999 |
| JP | 11-226408 A | 8/1999 |
| JP | 2000-500699 A | 1/2000 |
| JP | 2000-126599 A | 5/2000 |
| JP | 2000-317309 A | 11/2000 |

OTHER PUBLICATIONS

Nilsson et al. "The Al . . . " CA 125:59183 (1966).*

* cited by examiner

*Primary Examiner*—Johann Richter
*Assistant Examiner*—Ebenezer Sackey
(74) *Attorney, Agent, or Firm*—Birch, Stewart, Kolasch & Birch, LLP

(57) ABSTRACT

Disclosed is an oxide catalyst comprising an oxide represented by the formula $Mo_1V_aNb_bX_cY_dZ_eQ_fO_n$ (wherein: X is at least one element selected from the group consisting of Te and Sb; Y is at least one element selected from the group consisting of Al and W; Z is at least one element selected from the group consisting of elements which individually form an oxide having a rutile structure and a Z oxide having a rutile structure is used as a source of Z for producing the catalyst; Q is at least one element selected from the group consisting of titanium, tin, germanium, lead, tantalum, ruthenium, rhenium, rhodium, iridium, platinum, chromium, manganese, technetium, osmium, iron, arsenic, cerium, cobalt, magnesium, nickel and zinc, and a Q compound not having a rutile structure is used as a source of Q for producing the catalyst; and a, b, c, d, e, f and n are, respectively, the atomic ratios of V, Nb, X, Y, Z, Q and O, relative to Mo). Also disclosed is a process for producing an unsaturated carboxylic acid or an unsaturated nitrile by using the above-mentioned oxide catalyst.

12 Claims, No Drawings

CATALYST FOR USE IN CATALYTIC OXIDATION OR AMMOXIDATION OF PROPANE OR ISOBUTANE IN THE GASEOUS PHASE

This application is a continuation-in-part of PCT Application No. PCT/JP01/05055, filed on Jun. 14, 2001, which designated the United States and on which priority is claimed under 35 U.S.C. §120.

BACKGROUND OF THE INVENTION

1. Field of the Invention

The present invention relates to an oxide catalyst for use in catalytic oxidation or ammoxidation of propane or isobutane in the gaseous phase. More particularly, the present invention is concerned with an oxide catalyst for use in a catalytic oxidation or ammoxidation of propane or isobutane in the gaseous phase, which comprises an oxide represented by the following formula (I):

$$Mo_1V_aNb_bX_cY_dZ_eQ_fO_n \qquad (I)$$

wherein X is at least one element selected from the group consisting of tellurium and antimony; Y is at least one element selected from the group consisting of aluminum and tungsten; Z is at least one element selected from the group consisting of elements which individually form an oxide having a rutile structure; Q is at least one element selected from the group consisting of titanium, tin, germanium, lead, tantalum, ruthenium, rhenium, rhodium, iridium, platinum, chromium, manganese, technetium, osmium, iron, arsenic, cerium, cobalt, magnesium, nickel and zinc; and a, b, c, d, e, f and n are, respectively, the atomic ratios of vanadium (V), niobium (Nb), X, Y, Z, Q and oxygen (O), relative to molybdenum (Mo), and wherein: $0.1 \leq a \leq 1.0$, $0.01 \leq b \leq 1.0$, $0.01 \leq c \leq 1.0$, $0 \leq d \leq 0.5$, $0 \leq e \leq 3$, $0 \leq f \leq 9$, with the proviso that $0 < d+e \leq 3.5$, and n is a number determined by and consistent with the valence requirements of the other elements present in the oxide of formula (I). By the use of the oxide catalyst of the present invention for the catalytic oxidation or ammoxidation of propane or isobutane in the gaseous phase, it becomes possible to improve the selectivity for the desired unsaturated carboxylic acid or unsaturated nitrile and to conduct an efficient production of the desired product. By virtue of these properties, the oxide catalyst of the present invention can be advantageously used in various industrial fields. The present invention is also concerned with a process for producing an unsaturated carboxylic acid or an unsaturated nitrile by using the above-mentioned oxide catalyst.

2. Prior Art

Acrylic acid and methacrylic acid (each of which is an unsaturated carboxylic acid), as well as acrylonitrile and methacrylonitrile (each of which is an unsaturated nitrile) are very important compounds in the industries. With respect to the method for producing these compounds, there is a well-known method in which propylene or isobutylene (each of which is an alkene (olefin)) is subjected to catalytic oxidation or catalytic ammoxidation in the gaseous phase to thereby obtain a corresponding unsaturated carboxylic acid or unsaturated nitrile.

Recently, attention has been attracted to a technique in which propane or isobutane (each of which is an alkane) is used as a substitute for the above-mentioned alkene. Specifically, an alkane is subjected to catalytic oxidation or catalytic ammoxidation in the gaseous phase to thereby produce a corresponding unsaturated carboxylic acid or unsaturated nitrile. A number of proposals have been made with respect to the methods for utilizing such a technique and the catalysts for use in such methods.

For example, EP 767164B, Unexamined Japanese Patent Application Laid-Open Specification Nos. 10-28862, 10-330343, 11-57479 and 11-226408, U.S. Pat. Nos. 6,036,880, 5,231,214, 5,281,745 and 5,472,925, EP 608838, Unexamined Japanese Patent Application Laid-Open Specification Nos. 10-45664, 10-57813 and 9-316023 disclose oxide catalysts which contain Mo, V, Nb and Sb (or Te) and additional elements, such as Ti, Al, W, Ta, Sn, Fe, Co and Ni.

In addition, EP 945432 A1 discloses an oxide catalyst containing Mo, V and Sb and additional elements, such as Ti, Sn, Fe, Cr, Ga, Li, Mg and Ca.

Further, U.S. Pat. Nos. 5,693,587, 5,854,172 and 5,972,833 disclose oxide catalysts which contain V and Sb and additional elements, such as Ti, Sn, Li, Mg, Na, Ca, Sr, Ba, Co and Fe.

When the oxide catalysts described in the above-mentioned publications are used for a catalytic oxidation or ammoxidation of propane or isobutane in the gaseous phase, the selectivity for the desired unsaturated carboxylic acid or unsaturated nitrile is unsatisfactory and, therefore, these oxide catalysts cannot be used for an efficient production of the desired product.

A carrier-supported catalyst (a catalyst comprising a compound having a catalytic activity and a carrier (such as silica) having supported thereon the compound) has high mechanical strength and is suitable for use in a fluidized-bed reactor. However, when a carrier-supported catalyst is prepared using the oxide catalysts disclosed in the above-mentioned publications, the selectivity for the desired products tends to be lowered. Therefore, the oxide catalysts disclosed in the above-mentioned publications have a problem in that the mode of the use of the oxide catalysts is limited.

For the reasons mentioned above, there is a strong demand for a development of an oxide catalyst which is capable of improving the selectivity for the desired products in a catalytic oxidation or ammoxidation of propane or isobutane.

SUMMARY OF THE INVENTION

In this situation, the present inventors have made extensive and intensive studies toward developing an oxide catalyst which exhibits an improved selectivity when the oxide catalyst is used for a catalytic oxidation or ammoxidation of propane or isobutane. As a result, it has unexpectedly been found that when catalytic oxidation or ammoxidation of propane or isobutane in the gaseous phase is conducted in the presence of an oxide catalyst containing a specific element in addition to Mo, V, Nb and Sb (or Te) (with respect to the oxide catalyst containing a certain type of the specific element, the oxide catalyst should be prepared using, as a source of the specific element in the oxide catalyst, an oxide of the specific element, which has a specific crystal structure), the selectivity for the desired product is improved. In addition, it has also been found that such an oxide catalyst can be advantageously used for preparing a carrier-supported catalyst.

The present invention has been completed, based on these novel findings.

Accordingly, it is a primary object of the present invention to provide an oxide catalyst for use in a catalytic oxidation or ammoxidation of propane or isobutane in the gaseous phase, which exhibits a high selectivity for a desired product.

Another object of the present invention is to provide a process for producing an unsaturated carboxylic acid or unsaturated nitrile by using the above-mentioned catalyst.

The foregoing and other objects, and advantages of the present invention will be apparent to those skilled in the art from the following detailed description taken in connection with the appended claims.

DETAILED DESCRIPTION OF THE INVENTION

In one aspect of the present invention, there is provided an oxide catalyst for use in catalytic oxidation or ammoxidation of propane or isobutane in the gaseous phase, which comprises an oxide represented by the following formula (I):

$$Mo_1V_aNb_bX_cY_dZ_eQ_fO_n \qquad (I)$$

wherein:
X is at least one element selected from the group consisting of tellurium and antimony;
Y is at least one element selected from the group consisting of aluminum and tungsten;
Z is at least one element selected from the group consisting of elements which individually form an oxide having a rutile structure;
Q is at least one element selected from the group consisting of titanium, tin, germanium, lead, tantalum, ruthenium, rhenium, rhodium, iridium, platinum, chromium, manganese, technetium, osmium, iron, arsenic, cerium, cobalt, magnesium, nickel and zinc; and
a, b, c, d, e, f and n are, respectively, the atomic ratios of vanadium (V), niobium (Nb), X, Y, Z, Q and oxygen (O), relative to molybdenum (Mo), wherein:
$0.1 \leq a \leq 1.0$,
$0.01 \leq b \leq 1.0$,
$0.01 \leq c \leq 1.0$,
$0 \leq d \leq 0.5$,
$0 \leq e \leq 3$,
$0 \leq f \leq 9$,
with the proviso that $0 < d+e \leq 3.5$, and
n is a number determined by and consistent with the valence requirements of the other elements present in the oxide of formula (I),
the oxide catalyst being produced by calcining a dried catalyst precursor, the precursor comprising:
(i) a molybdenum (Mo) compound which does not have a rutile structure;
(ii) a vanadium (V) compound which does not have a rutile structure;
(iii) a niobium (Nb) compound which does not have a rutile structure;
(iv) at least one X compound selected from the group consisting of compounds of elements defined as X in formula (I), wherein the X compound does not have a rutile structure;
(v) at least one compound selected from the group consisting of the following compounds (V-1) and (v-2):
(v-1) at least one Y compound selected from the group consisting of compounds of elements defined as Y in formula (I), wherein the Y compound does not have a rutile structure, and
(v-2) at least one Z oxide selected from the group consisting of oxides of elements defined as Z in formula (I), wherein the Z oxide has a rutile structure; and optionally
(vi) at least one Q compound selected from the group consisting of compounds of elements defined as Q in formula (I), wherein the Q compound does not have a rutile structure.

For easy understanding of the present invention, the essential features and various preferred embodiments of the present invention are enumerated below.

1. An oxide catalyst for use in catalytic oxidation or ammoxidation of propane or isobutane in the gaseous phase, which comprises an oxide represented by the following formula (I):

$$Mo_1V_aNb_bX_cY_dZ_eQ_fO_n \qquad (I)$$

wherein:
X is at least one element selected from the group consisting of tellurium and antimony;
Y is at least one element selected from the group consisting of aluminum and tungsten;
Z is at least one element selected from the group consisting of elements which individually form an oxide having a rutile structure;
Q is at least one element selected from the group consisting of titanium, tin, germanium, lead, tantalum, ruthenium, rhenium, rhodium, iridium, platinum, chromium, manganese, technetium, osmium, iron, arsenic, cerium, cobalt, magnesium, nickel and zinc; and
a, b, c, d, e, f and n are, respectively, the atomic ratios of vanadium (V), niobium (Nb), X, Y, Z, Q and oxygen (O), relative to molybdenum (Mo), wherein:
$0.1 \leq a \leq 1.0$,
$0.01 \leq b \leq 1.0$,
$0.01 \leq c \leq 1.0$,
$0 \leq d \leq 0.5$,
$0 \leq e \leq 3$,
$0 \leq f \leq 9$,
with the proviso that $0 < d+e \leq 3.5$, and
n is a number determined by and consistent with the valence requirements of the other elements present in the oxide of formula (I),
the oxide catalyst being produced by calcining a dried catalyst precursor, the precursor comprising:
(i) a molybdenum (Mo) compound which does not have a rutile structure;
(ii) a vanadium (V) compound which does not have a rutile structure;
(iii) a niobium (Nb) compound which does not have a rutile structure;
(iv) at least one X compound selected from the group consisting of compounds of elements defined as X in formula (I), wherein the X compound does not have a rutile structure;
(v) at least one compound selected from the group consisting of the following compounds (v-1) and (v-2):
(v-1) at least one Y compound selected from the group consisting of compounds of elements defined as Y in formula (I), wherein the Y compound does not have a rutile structure, and
(v-2) at least one Z oxide selected from the group consisting of oxides of elements defined as Z in formula (I),
wherein the Z oxide has a rutile structure; and optionally (vi) at least one Q compound selected from the group consisting of compounds of elements defined as Q in formula (I), wherein the Q compound does not have a rutile structure.

2. The oxide catalyst according to item 1 above, wherein X in formula (I) is antimony.

3. The oxide catalyst according to item 1 or 2 above, wherein Y in formula (I) is aluminum and the compound (v-1) is aluminum oxide.

4. The oxide catalyst according to any one of items 1 to 3 above, wherein Z in formula (I) is at least one element selected from the group consisting of titanium and tin.

5. The oxide catalyst according to any one of items 1 to 4 above, which further comprises a silica carrier having supported thereon the oxide, wherein the silica carrier is present in an amount of from 20 to 60% by weight in terms of $SiO_2$, based on the total weight of the oxide and the silica carrier in terms of $SiO_2$.

6. The oxide catalyst according to any one of items 1 to 5 above, wherein the dried catalyst precursor further comprises a dicarboxylate value.

7. The oxide catalyst according to any one of items 1 to 6 above, wherein the calcination is performed in an inert gas atmosphere which is substantially free from molecular oxygen.

8. The oxide catalyst according to any one of items 1 to 7 above, wherein the dried catalyst precursor is produced by a method comprising the following steps (1) and (2):

(1) providing a solution or slurry of a raw material mixture in an aqueous medium, the raw material mixture comprising the compounds (i) to (vi); and (2) drying the raw material mixture solution or slurry obtained in step (1), to thereby obtain the dried catalyst precursor.

9. The oxide catalyst according to item 8 above, wherein, in step (1) of providing the raw material mixture solution or slurry, the niobium compound (iii) is used in the form of a niobium-containing aqueous solution comprising water having dissolved therein a dicarboxylic acid and the niobium compound (iii), wherein the molar ratio of the dicarboxylic acid to the niobium compound (iii) in terms of niobium is from 1 to 8.

10. The oxide catalyst according to item 9 above, wherein the niobium-containing aqueous solution further comprises hydrogen peroxide, wherein the molar ratio of the hydrogen peroxide to the niobium compound (iii) in terms of niobium is from 0.5 to 10.

11. A process for producing acrylic acid or methacrylic acid, which comprises reacting propane or isobutane with molecular oxygen in the gaseous phase in the presence of the oxide catalyst of any one of items 1 to 10 above.

12. A process for producing acrylonitrile or methacrylonitrile, which comprises reacting propane or isobutane with ammonia and molecular oxygen in the gaseous phase in the presence of the oxide catalyst of any one of items 1 to 10 above.

The present invention will now be described in detail.

The oxide catalyst of the present invention is an oxide catalyst for use in a catalytic oxidation or ammoxidation of propane or isobutane in the gaseous phase, and it comprises an oxide represented by the following formula (I):

$$Mo_1V_aNb_bX_cY_dZ_eQ_fO_n \qquad (I).$$

In formula (I), X is at least one element selected from the group consisting of tellurium and antimony. It is preferred that the X element is antimony.

Y is at least one element selected from the group consisting of aluminum and tungsten. It is preferred that the Y element is aluminum.

Z is at least one element selected from the group consisting of elements which individually form an oxide having a rutile structure.

The rutile structure is one type of crystal structures, which is frequently observed in an $AB_2$-type compound (wherein A is a metal element and B is an electro-negative element, such as oxygen and fluorine). A representative example of an $AB_2$-type compound having a rutile structure is rutile, which is one form of titanium dioxide ($TiO_2$).

In the rutile structure observed in an $AB_2$-type compound, A elements are positioned at the apices and center of the tetragonal lattice, and each A element is surrounded by six B elements, wherein the six B elements are arranged in an octahedron configuration and wherein the A element (surrounded by six B elements) is positioned at the center of the octahedron. For the details of the rutile structure, reference can be made to various publications, for example, Encyclopaedia Chimica (published by KYORITSU SHUPPAN CO., LTD., Japan 1993).

As the Z elements which are capable of forming oxides having a rutile structure, there can be mentioned not only an element which is capable of forming by itself alone an oxide having a rutile structure, but also an element which is incapable of forming by itself alone an oxide having a rutile structure, but is capable of forming, in cooperation with another element, a compound oxide having a rutile structure. Such compound oxides include a compound oxide having a statistical rutile structure (also called a random rutile structure) and a compound oxide having a trirutile structure.

As specific examples of Z elements, there can be mentioned titanium, tin, germanium, lead, tantalum, ruthenium, rhenium, rhodium, iridium, platinum, molybdenum, vanadium, niobium, tellurium, antimony, aluminum, tungsten and the like. It is preferred that the Z element is at least one element selected from the group consisting of titanium and tin.

Q is at least one element selected from the group consisting of titanium, tin, germanium, lead, tantalum, ruthenium, rhenium, rhodium, iridium, platinum, chromium, manganese, technetium, osmium, iron, arsenic, cerium, cobalt, magnesium, nickel and zinc. The above-mentioned Q elements may form an oxide having a rutile structure. However, as explained below in detail, the compound used as a source of the Q element for producing the oxide catalyst of the present invention (i.e., Q compound (vi) mentioned below) does not have a rutile structure, whereas the compound (oxide) used as a source of the Z element for producing the oxide catalyst of the present invention (i.e., Z oxide (v-2) mentioned below) has a rutile structure.

It is preferred that the Q element is at least one element selected from the group consisting of titanium, tin, lead, chromium, manganese, iron, cerium, cobalt, magnesium, nickel and zinc, and at least one element selected from the group consisting of titanium, tin and lead is more preferred.

a, b, c, d, e and f are, respectively, the atomic ratios of vanadium (V), niobium (Nb), X, Y, Z and Q. As explained below in detail, these values are determined by the ratio of the raw material compounds used for producing the oxide catalyst.

a satisfies the relationship $0.1 \leq a \leq 1.0$. It is preferred that a is in a range of from 0.2 to 0.5, more preferably from 0.2 to 0.4.

b satisfies the relationship $0.01 \leq b \leq 1.0$. It is preferred that b is in a range of from 0.01 to 0.2, more preferably from 0.02 to 0.15.

c satisfies the relationship $0.01 \leq c \leq 1.0$. It is preferred that c is in a range of from 0.1 to 0.5, more preferably from 0.1 to 0.4.

d satisfies the relationship $0 \leq d \leq 0.5$. It is preferred that d is in a range of from 0 to 0.3, more preferably from 0 to 0.2.

e satisfies the relationship $0 \leq e \leq 3$. It is preferred that e is in a range of from 0 to 2, more preferably from 0 to 1.

f satisfies the relationship $0 \leq f \leq 9$. It is preferred that f is in a range of from 0 to 3, more preferably from 0 to 0.3.

With respect to d and e, it is required that d and e satisfy the relationship $0 < d+e \leq 3.5$.

n is a number determined by and consistent with the valence requirements of the other elements present in the oxide of formula (I).

It is preferred that the oxide catalyst of the present invention further comprises a silica carrier having supported thereon the oxide. That is, the oxide catalyst of the present invention is preferably a silica-supported oxide catalyst. The mechanical strength of the oxide catalyst increases when the oxide catalyst of the present invention is made into a silica-supported oxide catalyst, and such a silica-supported oxide catalyst can be advantageously used for the gaseous phase catalytic oxidation and the gaseous phase catalytic ammoxidation in a fluidized-bed reactor. The silica carrier is present in an amount of from 20 to 60% by weight in terms of $SiO_2$, preferably from 30 to 50% by weight, based on the total weight of the oxide represented by formula (I) above and the silica carrier in terms of $SiO_2$.

The oxide catalyst of the present invention is produced by calcining a dried catalyst precursor comprising:
(i) a molybdenum (Mo) compound which does not have a rutile structure;
(ii) a vanadium (V) compound which does not have a rutile structure;
(iii) a niobium (Nb) compound which does not have a rutile structure;
(iv) at least one X compound selected from the group consisting of compounds of elements defined as X in formula (I), wherein the X compound does not have a rutile structure;
(v) at least one compound selected from the group consisting of the following compounds (v-1) and (v-2):
  (v-1) at least one Y compound selected from the group consisting of compounds of elements defined as Y in formula (I), wherein said Y compound does not have a rutile structure, and
  (v-2) at least one Z oxide selected from the group consisting of oxides of elements defined as Z in formula (I), wherein said Z oxide has a rutile structure; and optionally
(vi) at least one Q compound selected from the group consisting of compounds of elements defined as Q in formula (I), wherein the Q compound does not have a rutile structure.

In the process of the present invention for producing an oxide catalyst comprising an oxide, the following compounds can be used as sources of the component elements of the oxide catalyst, that is, as the above-mentioned compounds (i) to (vi).

Examples of compound (i) include ammonium heptamolybdate, molybdenum oxides, molybdenum oxychlorides, molybdenum chlorides, molybdenum alkoxides and the like. Of these, hexavalent molybdenum compounds, especially ammonium heptamolybdate is preferred.

A molybdenum compound having a rutile structure cannot be used as the above-mentioned compound (i).

Examples of compound (ii) include ammonium metavanadate, vanadium (V) oxide, vanadium oxychlorides, vanadium alkoxides and the like. Of these, pentavalent vanadium compounds, especially ammonium metavanadate is preferred.

A vanadium compound having a rutile structure cannot be used as the above-mentioned compound (ii).

Examples of compound (iii) include niobic acid, an inorganic acid salt of niobium, and an organic acid salt of niobium. Among these niobium compounds, it is preferred to use a niobic acid. The "niobic acid" is a hydrated compound represented by the following formula: $Nb_2O_5 \cdot nH_2O$, which is also known as "niobium hydroxide" or "niobium oxide hydrate".

A niobium compound having a rutile structure cannot be used as the above-mentioned compound (iii).

The compound (iv) is a compound of the elements defined as X in formula (I), that is, at least one compound selected from the group consisting of compounds of tellurium and the compounds of antimony.

Specific examples of tellurium compounds include inorganic tellurium compounds, such as telluric acid ($H_6TeO_6$), tellurium dioxide and tellurium trioxide; and organic tellurium compounds, such as methyltellurol and dimethyl telluroxide. Among these, telluric acid is preferred.

A tellurium compound having a rutile structure cannot be used as the above-mentioned compound (iv).

Examples of antimony compounds include antimony (III) oxide; antimony (III) antimony (V) oxide; antimony (III) chloride; antimony (III) oxychloride; antimony (III) nitrate oxide; organic acid salts of antimony, such as antimony tartrate; antimony alkoxides and the like. Of these, trivalent antimony compounds, especially antimony (III) oxide is preferred.

An antimony compound having a rutile structure cannot be used as the above-mentioned compound (iv).

The above-mentioned compound (v) is at least one compound selected from the group consisting of the following compounds (v-1) and (v-2):
  (v-1) at least one Y compound selected from the group consisting of compounds of elements defined as Y in formula (I), wherein the Y compound does not have a rutile structure, and
  (v-2) at least one Z oxide selected from the group consisting of oxides of elements defined as Z in formula (I), wherein the Z oxide has a rutile structure.

The compound (v-1) is a compound of the elements defined as Y in formula (I), that is, at least one compound selected from the group consisting of aluminum compounds and tungsten compounds.

Examples of aluminum compounds include aluminum oxide; aluminum hydroxide; aluminum nitrate; aluminum halides, such as aluminum chloride; aluminum alkoxides, such as aluminum ethoxide; aluminum acetate; aluminum lactate; aluminum laurate and aluminum acetylacetate. Of these, aluminum oxide, aluminum hydroxide and aluminum nitrate are preferred, and aluminum oxide, especially α-alumina, is more preferred.

Aluminum oxide can be prepared by calcining aluminum hydroxide, aluminum nitrate or aluminum. It is preferred that the calcination is conducted at 600 to 1500° C., more preferably 800 to 1400° C.

An aluminum compound having a rutile structure cannot be used as the above-mentioned compound (v-1).

Examples of tungsten compounds include ammonium paratungstate, ammonium metatungstate and tungsten trioxide. Of these, ammonium metatungstate is especially preferred.

A tungsten compound having a rutile structure cannot be used as the above-mentioned compound (v-1).

At least one Z oxide (v-2) is selected from the group consisting of oxides of elements defined as Z in formula (I), wherein the Z oxide has a rutile structure.

For example, the oxides of titanium include TiO, $Ti_2O_3$, $TiO_2$ and the like, but only $TiO_2$ is capable of forming a rutile structure. Therefore, when titanium is used as the Z element, rutile $TiO_2$ is used as Z oxide (v-2).

Further, a compound oxide containing two or more types of Z elements and having a rutile structure can be used as Z oxide (v-2). Such a compound oxide may have a statistical rutile structure or a trirutile structure. Examples of such compound oxides include $FeSbO_4$, $AlSbO_4$ and the like.

A compound oxide having a rutile structure can be produced by conventional methods, for example by the following methods (a) to (d):

(a) a method in which oxides of the component elements of the compound oxide are mixed in a ball mill or the like, and the resultant mixture is calcined;

(b) a method in which aqueous solutions each containing the component element(s) of the compound oxide are mixed together to thereby obtain a precipitate containing the component elements of the compound oxide, and the obtained precipitate is collected and calcined;

(c) a method in which aqueous solutions each containing the component element(s) of the compound oxide (and, if desired, an insoluble compound containing the component element of the compound oxide) are mixed together, the resultant aqueous mixture (solution or dispersion) is spray dried or evaporation-dried to thereby obtain dried particles, and the obtained particles are calcined; and (d) a method in which an aqueous mixture (solution or dispersion) containing the component elements of the compound oxide is subjected to a hydrothermal reaction.

In the above-mentioned methods (a) to (c), the calcination temperature is preferably 400 to 1500° C., more preferably 600 to 1000° C. The calcination time is preferably 1 to 200 hours. In method (a), the calcination time is preferably 50 to 150 hours, and in methods (b) and (c), the calcination time is preferably 1 to 10 hours. Further, the calcination may be performed in any atmosphere, for example, in an atmosphere of air or an inert gas, or under a vacuum.

The rutile structure of Z oxide (v-2) can be confirmed by a conventional method, for example by an X-ray diffraction analysis. A large amount of X-ray diffraction data on crystalline inorganic compounds (namely, data on the positions and relative intensities of peaks in an X-ray diffraction pattern) are conventionally known (see, for example, Powder Diffraction File (published by International Centre for Diffraction Data, U.S.A.)). Therefore, the rutile structure of Z oxide (v-2) can be easily confirmed by comparing the X-ray diffraction data of Z oxide (v-2) with the conventional data.

Z oxide (v-2) used in the present invention is usually in a microparticulate form. The preferred average diameter of particles of Z oxide (v-2) is 0.05 to 0.5 µm. There is no particular limitation with respect to the morphology of the particles of Z oxide (v-2), and the particles having any morphology, such as spherical particles, quasi-spherical particles, spindle-shaped particles and dendritic particles, can be used. Among these morphologies, spherical particles and quasi-spherical particles are preferred.

When Z oxide (v-2) is used as compound (v), Z oxide (v-2) is mixed with other raw materials to thereby obtain a solution or slurry of a raw material mixture, and the obtained solution or slurry of the raw material mixture is subjected to the below-mentioned drying process and calcination process, to thereby obtain the oxide catalyst of the present invention which exhibits an improved selectivity for the desired product in a catalytic oxidation or ammoxidation in the gaseous phase. No improvement in selectivity for the desired product in a catalytic oxidation or ammoxidation of propane or isobutane in the gaseous phase is achieved by an oxide catalyst which is produced by merely physically mixing Z oxide (v-2) and Mo—V—Nb—X type (X is Sb and/or Te) oxide catalyst which contains no Z element.

The above-mentioned compound (vi) is at least one Q compound selected from the group consisting of compounds of elements defined as Q in formula (I), i.e., at least one compound selected from the group consisting of compounds of titanium, tin, germanium, lead, tantalum, ruthenium, rhenium, rhodium, iridium, platinum, chromium, manganese, technetium, osmium, iron, arsenic, cerium, cobalt, magnesium, nickel and zinc, wherein the Q compound does not have a rutile structure.

Examples of Q compounds include oxides, hydroxides, inorganic acid salts, organic acid salts, ammonium salts, carbonates and alkoxides of the Q elements and the like.

A Q compound having a rutile structure cannot be used as the above-mentioned compound (vi).

When Q compound (vi) is used in combination with Z oxide (v-2), it is preferred that the ratio (hereinafter, referred to as "$C_{v-2}$") of the molar amount of Z oxide (v-2) to the total molar amounts of Z oxide (v-2) and compound (vi), wherein the molar amount of Z oxide (v-2) and the molar amount of Q compound (vi) are, respectively, given in terms of Z element and Q element, is at least 25%, more preferably at least 50%, and most preferably at least 90%.

In other words, it is preferred that e and f in formula (I) above satisfy the following relationship:

$e/(e+f) \leq 0.25$, more preferably $e/(e+f) \leq 0.50$, and most preferably $e/(e+f) \leq 0.90$.

The above-mentioned ratio $C_{v-2}$ can be determined from an X-ray diffraction pattern of a mixture containing Q compound (vi) and Z oxide (v-2), namely, from the ratio of the areas of peaks in an X-ray diffraction pattern.

First, using a plurality of standard sample mixtures of Z oxide (v-2) and Q compound (vi) each having a predetermined $CI_{v-2}$ value, a calibration curve showing the relationship between $C_{v-2}$ and the ratio of the areas of peaks in an X-ray diffraction pattern of the standard sample mixture is prepared.

An X-ray diffraction pattern of one standard sample mixture of Z oxide (v-2) and Q compound (vi) having a predetermined $C_{v-2}$ value is obtained. Among the peaks observed in the obtained X-ray diffraction pattern, one peak ascribed to the Z oxide (v-2) (hereinafter referred to as "Z peak") and one peak ascribed to the Q compound (vi) (hereinafter referred to as "Q peak") are arbitrarily selected, with the proviso that the Z peak does not overlap with Q peak.

Then, the area $A_{v-2}$ of the Z peak and the area $A_{vi}$ of the Q peak are determined, and the ratio $R_{v-2}$ (which is the ratio of $A_{v-2}$ to the total area of $A_{v-2}$ and $A_{vi}$) is calculated in accordance with the following formula:

$R_{v-2} = A_{v-2}/(A_{2-v} + A_{vi})$

The above-mentioned procedure is repeated while changing the $C_{2-v}$ of the standard sample mixture. Specifically, with respect to the X-ray diffraction pattern of each of the standard sample mixtures, the ratio $R_{v-2}$ is calculated based on the area $A_{2-v}$ (i.e., the area of a peak observed at the same diffraction angle 2θ as that of the Z peak) and the area $A_{vi}$ (i.e., the area of a peak observed at the same diffraction angle 2θ as that of the Q peak) so as to obtain a plurality of $R_{2-v}$ values.

The above-obtained $R_{2-v}$ values are plotted against the $C_{2-v}$ values so as to prepare a calibration curve showing the relationship between $C_{v-2}$ and $R_{v-2}$.

Using the thus obtained calibration curve, the $C_{v-2}$ of a sample can be determined from the $R_{v-2}$ calculated based on the areas $A_{v-2}$ and $A_{vi}$ in the X-ray diffraction pattern of the sample.

The above-mentioned technique can be applied to a case wherein the z element and the Q element are the same element. For example, with respect to a mixture of rutile $TiO_2$ (z oxide (v-2)) and anatase $TiO_2$ (Q compound (vi)), the ratio $C_R$ (corresponding to the $C_{v-2}$ above) of the molar amount of the rutile $TiO_2$ (in terms of titanium) to the total molar amount of the rutile $TiO_2$ and anatase $TiO_2$ (both in terms of titanium) can be determined as follows, using a plurality of standard sample mixtures of rutile $TiO_2$ and anatase $TiO_2$ each having a predetermined $C_R$ value.

An X-ray diffraction pattern of one standard sample mixture of rutile $TiO_2$ and anatase $TiO_2$ having a predetermined $C_R$ value is obtained.

In an X-ray diffraction pattern of rutile $TiO_2$, a strong peak is observed at 27.42° (2θ). On the other hand, in an X-ray diffraction pattern of anatase $TiO_2$, a strong peak is observed at 25.28° (2θ). Therefore, in the obtained X-ray diffraction pattern, characteristic peaks are observed at 27.420 (2θ) (ascribed to rutile $TiO_2$) and at 25.28° (2θ) (ascribed to anatase $TiO_2$).

Then, the area $A_{27.42}$ of the peak observed at 27.42° (2θ) and the area $A_{25.28}$ of the peak observed at 25.28° (2θ) are determined, and the ratio $R_{27.42}$ (which is the ratio of $A_{27.42}$ to the total area of $A_{27.42}$ and $A_{25.28}$) is calculated in accordance with the following formula:

$$R_{27.42} = A_{27.42}/(A_{27.42} + A_{25.28}).$$

The above-mentioned procedure is repeated while changing the $C_R$ of the standard sample mixture. Specifically, with respect to the X-ray diffraction pattern of each of the standard sample mixtures, the ratio $R_{27.42}$ is calculated based on the area $A_{27.42}$ (i.e., the area of a peak observed at 27.42° (2θ)) and the area $A_{25.28}$ (i.e., the area of a peak observed at 25.28° (2θ) ) so as to obtain a plurality of $R_{27.42}$ values.

The above-obtained $R_{27.42}$ values are plotted against the $C_R$ values so as to prepare a calibration curve showing the relationship between $C_R$ and $R_{27.42}$.

Using the thus obtained calibration curve, the $C_R$ of a sample can be determined from the $R_{27.42}$ calculated based on the areas $A_{27.42}$ and $A_{25.28}$ in the X-ray diffraction pattern of the sample.

In many cases, the $C_{v-2}$ for the other combinations of Z oxide (v-2) and Q compound (vi) can be determined in substantially the same manner as mentioned above.

However, when Z oxide (v-2) is a compound oxide containing 2 or more Z elements and having a rutile structure, it is difficult to determine an accurate $C_{v-2}$ thereof.

Therefore, in the present invention, when Z oxide (v-2) is a compound oxide having a rutile structure, $C_{v-2}$ is determined by the following simplified method.

An X-ray diffraction pattern of a mixture containing Z oxide (v-2) (which is a compound oxide having a rutile structure) is obtained. With respect to the obtained X-ray diffraction pattern, the total area of the peaks ascribed to the Z oxide (v-2) and the total area of the peaks observed at a diffraction angle (2θ) within the range of from 10 to 60° are determined. The ratio of the former total area to the latter total area is defined as $C_{v-2}$.

In this case, when a peak ascribed to the Z oxide (v-2) overlaps with a peak ascribed to a compound other than the Z oxide (v-2), the overlapping peak is considered as a peak ascribed to the Z oxide (v-2).

Since data on the positions and relative intensities of peaks in an X-ray diffraction pattern are available with respect to a large number of crystalline inorganic compounds (for example, reference can be made to the above-mentioned Powder Diffraction File (published by International Centre for Diffraction Data, U.S.A.)), a person skilled in the art can easily distinguish a peak ascribed to a compound oxide having a rutile structure from a peak ascribed to a compound other than the compound oxide.

In this method, amounts of non-crystalline substances contained in the mixture are not taken into consideration. However, usually, the amounts of such non-crystalline substances are very small. Therefore, no problem occurs even when ignoring of the non-crystalline substances.

The suitable amounts of the compounds (i) to (vi) vary depending on the types of the compounds used, and the amounts are appropriately selected so that an oxide having the composition represented by formula (I) is obtained.

When at least one element selected from the group consisting of molybdenum, vanadium and niobium is used as Z element, it is required that an oxide of at least one element selected from the group consisting of molybdenum, vanadium and niobium, which has a rutile structure is used as Z oxide (v-2) in combination with a molybdenum compound which does not have a rutile structure as compound (i), a vanadium compound which does not have a rutile structure as compound (ii) and a niobium (Nb) compound which does not have a rutile structure as compound (iii).

Therefore, for example, when vanadium is used as Z element, it is required that in the production of the oxide catalyst of the present invention, a vanadium oxide (or a vanadium-containing compound oxide) having a rutile structure (for example, vanadium (VI) dioxide) as Z oxide (v-2) is used in combination with a vanadium compound which does not have a rutile structure (for example, ammonium metavanadate) as compound (ii). In this case, the amount of the vanadium compound as compound (ii) is selected so that "a" in formula (I) above satisfies the relationship $0.1 \leq a \leq 1.0$, and the amount of the vanadium oxide (or vanadium-containing compound oxide) as Z oxide (v-2) is selected so that "e" in formula (I) above satisfies the relationship $0 \leq e \leq 3$.

When at least one element selected from the group consisting of tellurium and antimony is used as Z element, it is required that an oxide of at least one element selected from the group consisting of tellurium and antimony, which has a rutile structure is used as Z oxide (v-2) in combination with an X compound which does not have a rutile structure (namely, a tellurium compound which does not have a rutile structure and/or an antimony compound which does not have a rutile structure) as compound (iv).

Therefore, for example, when antimony is used as Z element, it is required that in the production of the oxide catalyst of the present invention, an antimony oxide (or an antimony-containing compound oxide) having a rutile structure (for example, AlSbO$_4$) as Z oxide (v-2) is used in combination with a tellurium compound which does not have a rutile structure (for example, telluric acid) and/or an antimony compound which does not have a rutile structure (for example, antimony (III) oxide) as compound (ii). In this case, the amount of the antimony compound as compound (iv) is selected so that "c" in formula (I) above satisfies the relationship $0.01 \leq c \leq 1.0$, and the amount of the antimony oxide (or antimony-containing compound oxide) as Z oxide (v-2) is selected so that "e" in formula (I) above satisfies the relationship $0 \leq e \leq 3$.

The oxide catalyst of the present invention, which comprises an oxide represented by formula (I) above, is obtained by calcining a dried catalyst precursor comprising the above-explained compounds (i) to (vi) (compound (vi) is an optional component), wherein the dried catalyst precursor is prepared by a method mentioned below.

The calcination can be conducted by a known method. For example, use can be made of a kiln, such as a rotary kiln, a tunnel kiln, a muffle kiln or a fluidized firing kiln. The calcination is generally conducted in an atmosphere of an inert gas, such as nitrogen gas under atmospheric pressure, which is substantially free of oxygen, preferably under a flow of an inert gas, at a temperature of 500 to 800° C., preferably 600 to 700° C. The time of calcination is generally 0.5 to 20 hours, preferably 1 to 8 hours. It is preferred that the oxygen concentration in the above-mentioned inert gas is 1000 ppm or less, more preferably 100 ppm or less as measured by gas chromatography or by means of a trace oxygen analyzer. The calcination can be conducted repeatedly. Prior to the calcination, the dried catalyst precursor may be subjected to pre-calcination in an atmosphere of air or under a stream of air at 200 to 400° C., preferably 250 to 350° C. for 1 to 5 hours. The catalyst obtained by calcination may be subjected to further calcination in an atmosphere of air at a temperature of from 200 to 400° C. for 5 minutes to 5 hours. The catalyst obtained by calcination may be pulverized and subjected to further calcination.

It is preferred that the above-mentioned dried catalyst precursor is produced by a method comprising the following steps (1) and (2):

(1) providing a solution or slurry of a raw material mixture in an aqueous medium, which comprises compounds (i) to (vi); and (2) drying the raw material mixture solution or slurry obtained in step (1), to thereby obtain the dried catalyst precursor.

Hereinbelow, the steps (1) and (2) will be described in more detail.

Step (1). Raw Material Mixture Preparation Step

In step (1), a solution or slurry of a raw material mixture comprising the compounds (i) to (vi) is provided by dissolving or dispersing the raw material mixture in an aqueous medium.

In the present invention, water is generally used as an aqueous medium, but in order to adjust the solubility of the compounds in the aqueous medium, use can be made of water containing an alcohol in an amount within a range which does not cause any adverse effect on the final oxide catalyst. Examples of alcohols used in the present invention include $C_{1-4}$ alcohols and benzyl alcohol. When a mixture of water and an alcohol is used as an aqueous medium, the ratio of water to the alcohol is appropriately selected, taking into consideration the solubility of the compounds contained in the raw material mixture in water and the alcohol.

With respect to the amount of the aqueous medium, there is no particular limitation as long as the amount of the aqueous medium is sufficient for forming a solution or slurry of the raw material mixture. However, from the viewpoint of the solubility of the respective raw material compounds of the component elements and the promotion of the reactions subsequently occurring in the aqueous medium (for example, the oxidation reaction occurring during the oxidizing treatment mentioned below), it is preferred to use 2 to 20 g of the aqueous medium per gram of the molybdenum compound (i.e., compound (i)) in the raw material mixture.

The suitable amounts of the compounds (i) to (vi) vary depending on the types of the compounds used, and the amounts are appropriately selected so that an oxide having the composition represented by formula (I) is obtained.

There is no particular limitation with respect to the method for preparing a raw material mixture by combining the above-mentioned compounds (i) to (vi), and a raw material mixture can be prepared by adding the above-mentioned compounds to an aqueous medium and mixing the resultant mixture. As specific examples of methods for preparing a raw material mixture, there can be mentioned the following methods.

In the explanation made below, each of the "aqueous mixtures $A^1$, $A^2$, $B^1$, $C^1$, $C^2$ and $C^3$" represents the mixtures defined below.

Aqueous mixture $A^1$: An aqueous mixture obtained by a method in which compound (i) (e.g., ammonium heptamolybdate), compound (ii) (e.g., ammonium metavanadate) and compound (iv) (e.g., antimony (III) oxide and/or tellurium oxide) are added to and mixed with an aqueous medium.

Aqueous mixture $A^2$: An aqueous mixture obtained by a method in which compound (i), compound (ii), compound (iv) and compound (v) (e.g., α-alumina and/or rutile titanium oxide) are added to and mixed with an aqueous medium.

Aqueous mixture $B^1$: An aqueous mixture obtained by a method in which compound (iii) (e.g., niobic acid) is added to and mixed with an aqueous medium.

Aqueous mixture $C^1$: An aqueous mixture obtained by a method in which compound (v-1) (e.g., α-alumina) and compound (v-2) (e.g., rutile titanium oxide) are added to and mixed with an aqueous medium.

Aqueous mixture $C^2$: An aqueous mixture obtained by a method in which compound (v-1) (e.g., α-alumina) is added to and mixed with an aqueous medium.

Aqueous mixture $C^3$: An aqueous mixture obtained by a method in which compound (v-2) (e.g., rutile titanium oxide) is added to and mixed with an aqueous medium.

Each of the above-mentioned aqueous mixtures is obtained as a solution or dispersion (including a slurry).

A raw material mixture can be obtained in the form of a solution or slurry by, for example, the following methods 1) to 4):

1) mixing predetermined amounts of the aqueous mixtures $A^1$, $B^1$ and $C^1$ together;

2) mixing predetermined amounts of the aqueous mixtures $A^1$, $B^1$, $C^2$ and $C^3$ together;

3) mixing predetermined amounts of the aqueous mixtures $A^1$, $B^1$ and $C^2$ (or $C^3$) together; or 4) mixing predetermined amounts of the aqueous mixtures $A^2$ and $B^1$ together.

Usually, the viscosity of the obtained slurry is relatively low and, thus, the slurry can be handled with ease.

When it is intended to provide an aqueous solution or slurry of a raw material mixture containing compound (vi), there is no particular limitation with respect to the timing to combine the compound (vi) with other compounds of the raw material mixture. For example, the compound (vi) can be added to any one of the above-mentioned aqueous mixtures $A^1$, $A^2$, $C^1$ and $C^3$. Alternatively, the compound (vi) can be added to the aqueous solution or slurry of the raw material mixture prepared in the above-mentioned manner.

When it is intended to produce a silica-supported catalyst, a silica sol can be added to any one of the aqueous mixtures mentioned above, or alternatively to a solution or slurry of the raw material mixture at any time in the above-mentioned step (1). The amount of silica in terms of $SiO_2$ is generally in the range of from 20 to 60% by weight, preferably 30 to 50% by weight, based on the total weight of the catalyst and silica. It is preferred to use a silica sol stabilized by ammonium ions to prevent gelation. It is preferred that the silica sol contains ammonium ions in an amount sufficient to keep the pH of the silica sol at around 9.7.

In the present invention, it is preferred to use, as aqueous mixture $B^1$, a niobium-containing aqueous solution which comprises water having dissolved therein a dicarboxylic acid and compound (iii) (e.g., niobic acid). When such an aqueous solution is used as aqueous mixture $B^1$, the properties of the final oxide catalyst are improved, as compared to an oxide catalyst produced using, as aqueous mixture $B^1$, a dispersion containing compound (iii). The improvements in properties of the oxide catalyst lead to an improvement in yield of the desired product of the catalytic oxidation reaction or catalytic ammoxidation reaction of propane or isobutane in the gaseous phase.

Examples of dicarboxylic acids used in the niobium-containing aqueous solution of the present invention include oxalic acid, tartaric acid, malonic acid, succinic acid and phthalic acid. Of these, oxalic acid is preferred.

Further, the molar ratio of the dicarboxylic acid to the niobium compound (iii) in terms of niobium (hereinafter, referred to as "dicarboxylic acid/Nb molar ratio") is preferably from 1 to 8, more preferably 1 to 6, still more preferably 2 to 4.

When a solution or slurry of a raw material mixture is produced using such a niobium-containing aqueous solution, at least a part of the dicarboxylic acid remains in the dried catalyst precursor.

As an example of a method for preparing the above-mentioned niobium-containing aqueous solution, there can be mentioned a method comprising the following steps (a) to (c):

(a) mixing water, a dicarboxylic acid (e.g., oxalic acid) and compound (iii) (e.g., niobic acid) to thereby obtain a preliminary niobium-containing aqueous solution or a niobium-containing aqueous semisolution having suspended therein a part of compound (iii);

(b) cooling the preliminary niobium-containing aqueous solution or niobium-containing aqueous semisolution to thereby precipitate a part of the dicarboxylic acid; and (c) removing the precipitated dicarboxylic acid from the preliminary niobium-containing aqueous solution, or removing the precipitated dicarboxylic acid and the suspended compound (iii) from the niobium-containing aqueous semisolution, thereby obtaining a niobium-containing aqueous solution.

The niobium-containing aqueous solution obtained in the above method usually has a dicarboxylic acid/Nb molar ratio within the range of from 2 to 4.

In this method, it is especially preferred that oxalic acid is used as the dicarboxylic acid. With respect to compound (iii) used in this method, there can be mentioned niobic acid and niobium hydrogenoxalate. These niobium compounds can be used in the form of a solid or in the form of a dispersion in an appropriate medium.

When niobium hydrogenoxalate is used as compound (iii), the dicarboxylic acid may not be used. When niobic acid is used as compound (iii), in order to remove acidic impurities with which the niobic acid may have been contaminated during the production thereof, the niobic acid may be washed with an aqueous ammonium solution and/or water prior to use.

It is preferred to use, as compound (iii), a freshly prepared niobium compound. However, in the above-mentioned method, a niobium compound can be used which is slightly denatured (for example by dehydration) as a result of a long-term storage and the like.

In step (a) of this method, the dissolution of compound (iii) can be promoted by the addition of a small amount of an aqueous ammonia or by heating.

The concentration of compound (iii) (in terms of niobium) in the preliminary aqueous solution or aqueous semisolution is preferably selected within the range of from 0.2 to 0.8 mol/kg of the solution or semi-solution. The dicarboxylic acid is preferably used in an amount such that the molar ratio of the dicarboxylic acid to compound (iii) in terms of niobium is approximately 3 to 6. When an excess amount of the dicarboxylic acid is used, a large amount of compound (iii) can be dissolved in the aqueous solution of dicarboxylic acid; however, a disadvantage is likely to arise in that the amount of the dicarboxylic acid which is caused to precipitate by cooling becomes too large, thus decreasing the utilization of the dicarboxylic acid. On the other hand, when an unsatisfactory amount of the dicarboxylic acid is used, a disadvantage is likely to arise in that a large amount of compound (iii) remains undissolved and is suspended in the aqueous solution of the dicarboxylic acid to form a semi-solution, wherein the suspended niobium compound is removed from the semisolution, thus decreasing the degree of utilization of compound (iii).

The cooling operation in step (b) is not particularly limited. The cooling can be performed simply, for example, by means of ice.

The removal of the precipitated dicarboxylic acid (or precipitated dicarboxylic acid and dispersed compound (iii)) in step (c) can be easily performed by a conventional method, for example, by decantation or filtration.

When the dicarboxylic acid/Nb molar ratio of the obtained niobium-containing aqueous solution is outside the range of from 2 to 4, either the compound (iii) or dicarboxylic acid may be added to the niobium-containing aqueous solution so that the dicarboxylic acid/Nb molar ratio of the solution falls within the above-mentioned range. However, in general, such an operation is unnecessary since a niobium-containing aqueous solution having the dicarboxylic acid/Nb molar ratio within the range of from 2 to 4 can be prepared by appropriately controlling the concentration of the compound (iii), the ratio of the dicarboxylic acid to the compound (iii) and the cooling temperature of the above-mentioned preliminary niobium-containing aqueous solution or semisolution.

An aqueous hydrogen peroxide solution may be added to the niobium-containing aqueous solution. The addition of an aqueous hydrogen peroxide solution prevents the precipitation of the compound (iii) during the long-term storage of the niobium-containing aqueous solution. In addition, the properties of the final oxide catalyst are improved, i.e., the space time yield during the catalytic oxidation reaction or catalytic ammoxidation reaction of propane or isobutane in the gaseous phase and the selectivity for the desired products are also improved.

When an aqueous hydrogen peroxide solution is used, the molar ratio of hydrogen peroxide to the compound (iii) in terms of niobium is preferably 0.5 to 10, more preferably 1 to 6.

Hydrogen peroxide may be added to the aqueous mixture $A^1$ or $A^2$ (both of these mixtures do not contain niobium) and the resultant mixture may be subjected to an oxidation treatment by agitating the resultant mixture at 30° C. to 70° C. for 30 minutes to 2 hours. The oxidation treatment leads to a further improvement in properties of the final oxide catalyst, and the space time yield during the catalytic oxidation reaction or catalytic ammoxidation reaction of propane or isobutane in the gaseous phase becomes improved.

The reason for the improvements is unclear, but it is considered to be as follows.

An oxide catalyst having especially excellent properties is obtained when use is made of aqueous mixture $A^1$ or $A^2$ in which compounds (i), (ii) and (iv) are dissolved in an aqueous medium and the oxidation states of molybdenum, vanadium and X element (tellurium and/or antimony) contained therein are satisfactorily high.

However, during the preparation of the aqueous mixture $A^1$ or $A^2$, an oxidation-reduction reaction may occur among molybdenum, vanadium and the X element. As a result of the oxidation-reduction reaction, the X element is oxidized, whereas the oxidation states of molybdenum and vanadium are lowered. When the aqueous mixture $A^1$ or $A^2$ containing molybdenum and vanadium (each having a lowered oxidation state) is used to produce an oxide catalyst, the properties of the oxide catalyst become unsatisfactory.

Therefore, it is considered that the oxide catalyst exhibits excellent properties when the aqueous mixture $A^1$ or $A^2$ is subjected to an oxidation treatment and the oxidation states of molybdenum and vanadium have been re-enhanced before use in the oxide catalyst.

When the oxidation treatment is conducted, it is preferred that the molar ratio of hydrogen peroxide to the compound (iv) in terms of the X element contained in the aqueous mixture $A^1$ or $A^2$ is from 0.01 to 5, more preferably from 0.5 to 3, still more preferably from 1 to 2.5.

Whether or not the oxidation treatment is conducted will depend on the type of X compound used as compound (iv).

For example, when antimony (III) oxide is used as the compound (iv), it is preferred to conduct the above-mentioned oxidation treatment. The reason is as follows. Antimony (III) oxide is difficult to dissolve in an aqueous medium. Therefore, in order to prepare aqueous mixture $A^1$ or $A^2$ in the form of a uniform solution, antimony (III) oxide must be converted, by the above-mentioned oxidation-reduction reaction, to a compound which is more soluble than antimony (III) oxide in an aqueous medium.

On the other hand, when telluric acid is used as the compound (iv), the oxidation treatment is unnecessary. Telluric acid is soluble in an aqueous medium. Therefore, telluric acid and the compounds (i) and (ii) can be easily dissolved in an aqueous medium by a method in which these compounds are simply added to and mixed with an aqueous medium without conducting the above-mentioned oxidation-reduction reaction.

Step (2). Drying Step

In step (2) of the process of the present invention, the above-mentioned solution or slurry of the raw material mixture is dried so as to obtain a dried catalyst precursor.

The drying of the solution or slurry of the raw material mixture can be conducted by a known method, such as spray drying or evaporation drying. The spray drying can be conducted, for example, by spraying and heating the solution or slurry of the raw material mixture in the dryer. The spray drying can be conducted by centrifugation, by the two-phase flow nozzle method or by the high pressure nozzle method. As a heat source for drying, it is preferred to use air which has been heated by steam, an electric heater and the like. It is preferred that the temperature of the dryer at an entrance to the dryer section thereof is from 150 to 300° C. The spray drying can be also conveniently conducted by spraying the solution or slurry of the raw material mixture onto an iron plate which has been heated to a temperature of 100 to 300° C.

The solution or slurry of the raw material mixture can be evaporation-dried by heating it in a vessel, such as a beaker, at 100 to 300° C. The time for heating varies depending on the composition or amount of the solution or slurry of the raw material, but is generally from 5 minutes to 20 hours, preferably from 5 minutes to 3 hours.

The dried catalyst precursor can be obtained in a powder form by the above-mentioned drying step.

The thus obtained dried catalyst precursor is calcined in the above-mentioned manner, to thereby obtain the oxide catalyst of the present invention which comprises the oxide represented by formula (I).

Acrylic acid or methacrylic acid can be produced by reacting propane or isobutane with molecular oxygen in the gaseous phase in the presence of the oxide catalyst obtained above. Acrylonitrile or methacrylonitrile can be produced by reacting propane or isobutane with ammonia and molecular oxygen in the gaseous phase in the presence of the oxide catalyst obtained above.

When the oxide catalyst of the present invention is used, it becomes possible to improve the selectivity for the desired unsaturated carboxylic acid or unsaturated nitrile in the catalytic oxidation or ammoxidation of propane or isobutane in the gaseous phase. The reason why the oxidation catalyst of the present invention exhibits excellent effects is unclear, but it is considered that the compounds of Y and/or Z elements, which are contained in the oxide catalyst of the present invention are responsible for the improvements in properties of the oxide catalyst.

An oxide catalyst which contains, in addition to Mo, V, Nb and Sb (or Te), an additional element other than these elements has been conventionally known. However, there is no publication which specifically describes an oxide catalyst containing the above-mentioned at least 5 elements (i.e., Mo, V, Nb, Sb (or Te) and an additional element). Therefore, in the past, the improvement in selectivity for the desired product in the catalytic oxidation or ammoxidation of propane or isobutane in the gaseous phase, which is brought by the use of the above-mentioned oxide catalyst was not known.

In addition, with respect to an oxide catalyst to be used for the catalytic oxidation or ammoxidation of propane or isobutane in the gaseous phase, there is no publication which describes the crystal structure of the compound used as a raw material for the oxide catalyst.

Hereinbelow, explanation is made with respect to the process for producing acrylic acid or methacrylic acid from propane or isobutane by oxidation in the gaseous phase in the presence of the oxide catalyst of the present invention, and the process for producing acrylonitrile or methacrylonitrile from propane or isobutane by ammoxidation in the gaseous phase in the presence of the oxide catalyst of the present invention.

The feedstock mixture comprising propane or isobutane and ammonia need not be of a very high purity but may be of a commercial grade.

Examples of sources of oxygen include air, oxygen-rich air, and pure oxygen. Further, such a source of molecular oxygen may be diluted with helium, argon, carbon dioxide, steam, nitrogen or the like.

The catalytic oxidation of propane or isobutane in the gaseous phase may be conducted under the following conditions.

The molar ratio of molecular oxygen to propane or isobutane used for the oxidation may be generally in the range of from 0.1 to 6, preferably from 0.5 to 4.

The oxidation temperature is generally in the range of from 300 to 500° C., preferably from 350 to 450° C.

The oxidation pressure is generally in the range of from $5 \times 10^4$ to $5 \times 10^5$ Pa, preferably from $1 \times 10^5$ to $3 \times 10^5$ Pa.

The time of contact (contact time) between the gaseous feedstocks and the catalyst is generally in the range of from 0.1 to 10 (g·sec/ml), preferably from 0.5 to 5 (g·sec/ml).

The catalytic ammoxidation of propane or isobutane in the gaseous phase may be conducted under the following conditions.

The molar ratio of molecular oxygen to propane or isobutane used for the ammoxidation may be generally in the range of from 0.1 to 6, preferably from 0.5 to 4.

The molar ratio of ammonia to propane or isobutane for the ammoxidation may be generally in the range of from 0.3 to 1.5, preferably from 0.8 to 1.0.

The ammoxidation temperature is generally in the range of from 350 to 500° C., preferably from 380 to 470° C.

The ammoxidation pressure is generally in the range of from $5 \times 10^4$ to $5 \times 10^5$ Pa, preferably from $1 \times 10^5$ to $3 \times 10^5$ Pa.

The time of contact (contact time) between the gaseous feedstocks and the catalyst is generally in the range of from 0.1 to 10 (g·sec/ml), preferably from 0.5 to 5 (g·sec/ml).

In the process of the present invention, the contact time is determined according to the following formula:

$$\text{Contact time (sec} \cdot \text{g/cc)} = \frac{W}{F} \times \frac{273}{273 + T}$$

wherein:

W represents the weight (g) of the catalyst contained in the reactor;

F represents the flow rate (Ncc/sec) of the raw material mixture gas {as measured under normal temperature and pressure conditions (0° C., $1.013 \times 10^5$ Pa)}; and T represents the reaction temperature (° C.).

The reaction of the present invention can be conducted in a conventional reactor, such as a fixed bed reactor, a fluidized-bed reactor or a moving bed reactor.

In the present invention, both the gaseous-phase catalytic oxidation reaction and the gaseous-phase catalytic ammoxidation reaction may be either a one pass mode or a recycling mode.

BEST MODE FOR CARRYING OUT THE INVENTION

Hereinbelow, the present invention will be described in more detail with reference to the following Examples and Comparative Examples, which should not be construed as limiting the scope of the present invention.

In the following Examples and Comparative Examples, the conversion (%) of propane and the selectivity (%) for acrylic acid, each used for evaluating the results of the oxidation of propane, are defined as follows:

$$\text{Conversion (\%) of propane} = \frac{\text{(moles of propane reacted)}}{\text{(moles of propane fed)}} \times 100$$

$$\text{Selectivity (\%) for acrylic acid} = \frac{\text{(moles of acrylic acid formed)}}{\text{(moles of propane reacted)}} \times 100$$

In the following Examples and Comparative Examples, the conversion (%) of propane and the selectivity (%) for acrylonitrile, each used for evaluating the results of the ammoxidation of propane, are defined as follows:

$$\text{Conversion (\%) of propane} = \frac{\text{(moles of propane reacted)}}{\text{(moles of propane fed)}} \times 100$$

$$\text{Selectivity (\%) for acrylonitrile} = \frac{\text{(moles of acrylonitrile formed)}}{\text{(moles of propane reacted)}} \times 100$$

The resultant gaseous reaction mixture was subjected to analysis by means of an online gas chromatography apparatus (GC-14B; manufactured and sold by Shimadzu Corporation, Japan).

EXAMPLE 1

Preparation of Aqueous Mixture A-1

1,964.9 g of ammonium heptamolybdate (($NH_4$)$_6$ $Mo_7O_{24}$·4$H_2O$), 416.7 g of ammonium metavanadate ($NH_4VO_3$), 373.1 g of antimony(III) oxide ($Sb_2O_3$) and 754.9 g of rutile titanium oxide ($TiO_2$) (in the form of quasi-spherical particles having an average particle diameter of 0.25 μm) were added to 13,620 g of water, and the resultant mixture was heated to about 90° C. for 2.5 hours under atmospheric pressure while stirring, to obtain a dispersion, and the obtained dispersion was cooled to about 70° C., to thereby obtain aqueous mixture A-1.

Preparation of Niobium-Containing Aqueous Solution B-1

To 5,630 g of water were added 860 g of niobic acid ($Nb_2O_5$ content: 80.2% by weight) and 3,270 g of oxalic acid dihydrate ($H_2C_2O_4$·2$H_2O$), and the resultant mixture was stirred at 95° C. for 1 hour, to thereby obtain a preliminary niobium-containing aqueous solution.

The obtained preliminary niobium-containing aqueous solution was allowed to stand still while cooling with ice, to thereby precipitate solids. The precipitated solids in the solution were removed from the aqueous solution by suction filtration, to thereby obtain a niobium-containing aqueous solution B-1.

Then, the niobic acid concentration in terms of niobium (hereinafter referred to as "niobium concentration") and oxalic acid concentration of the aqueous solution B-1 were determined.

First, the niobium concentration of the aqueous solution B-1 was determined as follows. A 10 g sample solution was accurately taken from the aqueous solution B-1 and charged into a crucible. The sample solution was dried overnight at 95° C., followed by calcination at 600° C. for 1 hour, thereby obtaining 0.8678 g of $Nb_2O_5$. As a result, it was found that the niobium concentration of the aqueous solution B-1 was 0.653 mol/kg of the aqueous solution.

Next, the oxalic acid concentration of the aqueous solution B-1 was determined as follows. To a 300 ml glass beaker was added 3 g of sample solution accurately taken from the aqueous solution B-1, followed by addition of 200 ml of water having a temperature of about 80° C. and 10 ml of aqueous sulfuric acid solution (volume ratio of concentrated sulfuric acid to water=1/1), to thereby obtain a test solution.

The obtained test solution was subjected to titration using ¼ N $KMnO_4$ solution, while stirring the test solution at 70° C. That is, the titration was conducted in accordance with the following reaction equation:

$$2KMnO_4 + 3H_2SO_4 + 5H_2C_2O_4$$

$$\rightarrow K_2SO_4 + 2MnSO_4 + 10CO_2 + 8H_2O.$$

An occurrence of a change in the color of the test solution in accordance with the progress of titration was examined. That is, the point at which the test solution was caused to assume a very light pink color due to the $KMnO_4$ and from which the test solution continued to have the very light pink color for 30 seconds or more, is defined as an end point of the titration. From the amount of ¼ N $KMnO_4$ solution consumed, the oxalic acid concentration of the aqueous solution B-1 was calculated using the above reaction formula. As a result, it was found that the oxalic acid concentration of the niobium-containing aqueous solution was 1.5607 mol/kg of the aqueous solution.

The above-mentioned analysis showed that the molar ratio of oxalic acid to niobic acid in terms of niobium (hereinafter referred to as "oxalic acid/Nb molar ratio") was 2.39.

Preparation of an Oxide Catalyst

An oxide catalyst comprising a silica carrier having supported thereon an oxide (silica carrier content: 43.2% by weight in terms of $SiO_2$, based on the total weight of the oxide and the silica carrier), in which the oxide is represented by the formula:

$$Mo_1V_{0.32}Nb_{0.07}S_{0.23}Ti_{0.85}O_n,$$

wherein n is a number determined by and consistent with the valence requirements of the other elements present in the oxide of the above formula, which applies to n appearing in the formulae representing the oxides obtained in all of the subsequent Examples and Comparative Examples, was prepared as follows.

To the above-mentioned aqueous mixture A-1 was added 7,843.1 g of a silica sol (having an $SiO_2$ content of 30.6% by weight) and then added 579.8 g of an aqueous hydrogen peroxide (having an $H_2O_2$ content of 15% by weight). The resultant mixture was subjected to oxidation treatment wherein the mixture was stirred at 50° C. for 1 hour, to thereby obtain an oxidized mixture.

In the above oxidation treatment, the molar ratio of hydrogen peroxide ($H_2O_2$) contained in the aqueous hydrogen peroxide used to antimony (Sb) contained in the raw material mixture solution (hereinafter, frequently referred to simply as "[$H_2O_2$:Sb] molar ratio") was 1.

To the obtained oxidized mixture was added 1,191.8 g of the above-mentioned niobium-containing aqueous solution B-1, to thereby obtain a slurry of a raw material mixture. The obtained slurry was easy to handle, because of the excellent dispersibility of the particles in the obtained slurry.

The obtained slurry was subjected to spray drying using a centrifugation type spray-drying apparatus under conditions wherein the inlet and outlet temperatures of the apparatus were 210° C. and 120° C., respectively, to thereby obtain a dried, microspherical particulate catalyst precursor.

480 g of the obtained dried catalyst precursor was charged into a SUS rotary kiln (inner diameter: 3 inch), and then calcined at 660° C. for 2 hours under a stream of nitrogen gas at a flow rate of 1,800 Ncc/min (Ncc means cc as measured under the normal temperature and pressure conditions, namely, at 0° C. under 1 atm.), to thereby obtain an oxide catalyst comprising an oxide of the above formula.

With respect to the oxygen concentration of the nitrogen gas used for the calcination, measurement was done by means of a trace oxygen analyzer (type 306WA; manufactured and sold by Teledyne Analytical Instruments, U.S.A.). As a result, it was found that the oxygen concentration of the nitrogen gas was 1 ppm.

Ammoxidation of Propane

Using the catalyst obtained above, an ammoxidation of propane was performed as follows.

45 g (W=45 g) of the obtained catalyst was charged into a Vycor glass fluidized-bed reaction tube having an inner diameter of 25 mm. In the reaction tube containing the catalyst, an ammoxidation of propane was performed under conditions wherein the temperature (T) was 440° C., the pressure (P) was atmospheric (i.e., 1 atm) and the contact time between the catalyst and a gaseous feedstock mixture (i.e., a gaseous mixture of propane, ammonia, molecular oxygen and helium, wherein the [propane:ammonia:molecular oxygen:helium] molar ratio was 1:0.6:1.5:5.6) was 3.0 g·sec/cc.

The results of the above ammoxidation are shown in Table 1.

COMPARATIVE EXAMPLE 1

Preparation of an Oxide Catalyst

An oxide catalyst comprising a silica carrier having supported thereon an oxide (silica carrier content: 50% by weight in terms of $SiO_2$, based on the total weight of the oxide and the silica carrier), in which the oxide is represented by the formula:

$$Mo_1VO_{0.32}Nb_{0.07}Sb_{0.23}O_n,$$

was prepared in substantially the same manner as in Example 1, except that in the preparation of the aqueous mixture A-1, 8,300 g of water was used and the addition of the titanium oxide was omitted.

Ammoxidation of Propane

An ammoxidation of propane was performed in the presence of the oxide catalyst obtained above under the same conditions as in Example 1. The results of the ammoxidation are shown in Table 1.

COMPARATIVE EXAMPLE 2

Preparation of an Oxide Catalyst

An oxide catalyst comprising a silica carrier having supported thereon an oxide (silica carrier content: 43.2% by weight in terms of $SiO_2$, based on the total weight of the oxide and the silica carrier), in which the oxide is represented by the formula:

$$Mo_1V_{0.32}Nb_{0.07}Sb_{0.23}Ti_{0.85}O_n,$$

was prepared in substantially the same manner as in Example 1, except that in the preparation of the aqueous mixture A-1, anatase titanium oxide (in the form of quasi-spherical particles having an average particle diameter of 0.1 μm) was used instead of rutile titanium oxide (in the form of quasi-spherical particles).

Ammoxidation of Propane

An ammoxidation of propane was performed in the presence of the oxide catalyst obtained above under the same conditions as in Example 1. The results of the ammoxidation are shown in Table 1.

COMPARATIVE EXAMPLE 3

Preparation of an Oxide Catalyst 1.72 g of the catalyst produced in Comparative Example 1 and 0.28 g of rutile titanium oxide were placed in a sample bottle and mixed. The thus obtained mixture was used as an oxide catalyst.

Ammoxidation of Propane

An ammoxidation of propane was performed in the presence of the oxide catalyst obtained above under the same conditions as in Example 1, except that the oxide catalyst was charged into a fixed-bed reactor having an inner diameter of 10 mm. The results of the ammoxidation are shown in Table 1.

EXAMPLE 2

Preparation of Aqueous Mixture A-2

1,964.9 g of ammonium heptamolybdate, 416.7 g of ammonium metavanadate, 373.1 g of antimony(III) oxide, 488.4 g of rutile titanium oxide (in the form of quasi-spherical particles having an average particle diameter of 0.25 μm) and 502.6 g of tin dioxide ($SnO_2$) (having a rutile structure) were added to 13,620 g of water, and the resultant mixture was heated to about 90° C. for 2.5 hours under atmospheric pressure while stirring, to obtain a dispersion, and the obtained dispersion was cooled to about 70° C., to thereby obtain aqueous mixture A-2.

Preparation of an Oxide Catalyst

An oxide catalyst comprising a silica carrier having supported thereon an oxide (silica carrier content: 41.4% by weight in terms of $SiO_2$, based on the total weight of the oxide and the silica carrier), in which the oxide is represented by the formula:

$$Mo_1V_{0.32}Nb_{0.07}Sb_{0.23}Ti_{0.55}Sn_{0.30}O_n,$$

was prepared as follows.

To the above-mentioned aqueous mixture A-2 was added 7,843.1 g of a silica sol (having an $SiO_2$ content of 30.6% by weight) and then added 579.8 g of an aqueous hydrogen peroxide (having an $H_2O_2$ content of 15% by weight). The resultant mixture was subjected to oxidation treatment wherein the mixture was stirred at 50° C. for 1 hour, to thereby obtain an oxidized mixture. In the above oxidation treatment, the [$H_2O_2$:Sb] molar ratio was 1.

To the obtained oxidized mixture was added 1191.8 g of the above-mentioned niobium-containing aqueous solution B-1, to thereby obtain a slurry of a raw material mixture. The obtained slurry was easy to handle, because of the excellent dispersibility of the particles in the obtained slurry.

The obtained slurry was subjected to spray drying using a centrifugation type spray-drying apparatus under conditions wherein the inlet and outlet temperatures of the apparatus were 210° C. and 120° C., respectively, to thereby obtain a dried, microspherical particulate catalyst precursor.

480 g of the obtained dried catalyst precursor was charged into a SUS rotary kiln (inner diameter: 3 inch), and then calcined at 660° C. for 2 hours under a stream of nitrogen gas at a flow rate of 1,800 Ncc/min, to thereby obtain an oxide catalyst comprising an oxide of the above formula.

With respect to the oxygen concentration of the nitrogen gas used for the calcination, measurement was done by means of a trace oxygen analyzer (type 306WA; manufactured and sold by Teledyne Analytical Instruments, U.S.A.). As a result, it was found that the oxygen concentration of the nitrogen gas was 1 ppm.

Ammoxidation of Propane

An ammoxidation of propane was performed in the presence of the oxide catalyst obtained above under the same conditions as in Example 1. The results of the ammoxidation are shown in Table 1.

EXAMPLE 3

Preparation of an Oxide Catalyst

An oxide catalyst comprising a silica carrier having supported thereon an oxide (silica carrier content: 39.6% by weight in terms of $SiO_2$, based on the total weight of the oxide and the silica carrier), in which the oxide is represented by the formula:

$$Mo_1V_{0.32}Nb_{0.07}Sb_{0.23}Ti_{0.85}Sn_{0.30}O_n$$

was prepared in substantially the same manner as in Example 2, except that in the preparation of the aqueous mixture A-2, 754.9 g of titanium oxide was used.

Ammoxidation of Propane

An ammoxidation of propane was performed in the presence of the oxide catalyst obtained above under the same conditions as in Example 1. The results of the ammoxidation are shown in Table 1.

EXAMPLE 4

Preparation of Aqueous Mixture A-3

1,964.9 g of ammonium heptamolybdate, 416.7 g of ammonium metavanadate and 373.1 g of antimony(III) oxide were added to 8,330 g of water, and the resultant mixture was heated to about 90° C. for 2.5 hours under atmospheric pressure while stirring, to obtain a solution, and the obtained solution was cooled to about 70° C., to thereby obtain aqueous mixture A-3.

Preparation of Niobium-containing Aqueous Solution B-2

Niobium-containing aqueous solution B-2 was prepared in same manner as in Example 1.

The niobic acid concentration of the aqueous solution B-2 in terms of niobium was 0.65 mol/kg of the aqueous solution, and the oxalic acid/Nb molar ratio was 2.38. These values were different from those of the niobium-containing aqueous solution B-1 prepared in Example 1, and the differences were caused by the difference in the amount of water which evaporated during the heating for dissolving niobic acid and oxalic acid in water.

The obtained niobium-containing aqueous solution B-2, as such, was used (i.e., without adjustment of the oxalic acid/Nb molar ratio) for preparing a catalyst.

Preparation of Aqueous Mixture C-1

754.9 g of rutile titanium oxide (in the form of quasi-spherical particles having an average particle diameter of 0.25 μm) was added to 5,290 g of water, and the resultant mixture was stirred, to thereby obtain aqueous mixture C-1.

Preparation of an Oxide Catalyst

An oxide catalyst comprising a silica carrier having supported thereon an oxide (silica carrier content: 43.2% by weight in terms of $SiO_2$, based on the total weight of the oxide and the silica carrier), in which the oxide is represented by the formula:

$Mo_1V_{0.32}Nb_{0.07}Sb_{0.23}Ti_{0.85}O_n$, was prepared as follows.

To the above-mentioned aqueous mixture A-3 was added 7,843.1 g of a silica sol (having an $SiO_2$ content of 30.6% by weight) and then added 579.8 g of an aqueous hydrogen peroxide (having an $H_2O_2$ content of 15% by weight). The resultant mixture was subjected to oxidation treatment wherein the mixture was stirred at 50° C. for 1 hour, to thereby obtain an oxidized mixture. In the above oxidation treatment, the [$H_2O_2$:Sb] molar ratio was 1.

To the obtained oxidized mixture were added 1,197.3 g of the above-mentioned niobium-containing aqueous solution B-2 and the above-prepared aqueous mixture C-1, to thereby obtain a slurry of a raw material mixture. The obtained slurry was easy to handle, because of the excellent dispersibility of the particles in the obtained slurry.

The obtained slurry was subjected to spray drying using a centrifugation type spray-drying apparatus under conditions wherein the inlet and outlet temperatures of the apparatus were 210° C. and 120° C., respectively, to thereby obtain a dried, microspherical particulate catalyst precursor.

480 g of the obtained dried catalyst precursor was charged into a SUS rotary kiln (inner diameter: 3 inch), and then calcined at 660° C. for 2 hours under a stream of nitrogen gas at a flow rate of 1,800 Ncc/min, to thereby obtain an oxide catalyst comprising an oxide of the above formula.

With respect to the oxygen concentration of the nitrogen gas used for the calcination, measurement was done by means of a trace oxygen analyzer (type 306WA; manufactured and sold by Teledyne Analytical Instruments, U.S.A.). As a result, it was found that the oxygen concentration of the nitrogen gas was 1 ppm.

Ammoxidation of Propane

An ammoxidation of propane was performed in the presence of the oxide catalyst obtained above under the same conditions as in Example 1. The results of the ammoxidation are shown in Table 1.

EXAMPLE 5

Preparation of an Oxide Catalyst

An oxide catalyst comprising a silica carrier having supported thereon an oxide (silica carrier content: 45.4% by weight in terms of $SiO_2$, based on the total weight of the oxide and the silica carrier), in which the oxide is represented by the formula:

$Mo_1V_{0.32}Nb_{0.07}Sb_{0.23}Ti_{0.55}O_n$, was prepared in substantially the same manner as in Example 4, except that in the preparation of the aqueous mixture C-1, 488.4 g of titanium oxide was used.

Ammoxidation of Propane

An ammoxidation of propane was performed in the presence of the oxide catalyst obtained above under the same conditions as in Example 1. The results of the ammoxidation are shown in Table 1.

EXAMPLE 6

Preparation of Aqueous Mixture A-4

1,964.9 g of ammonium heptamolybdate, 416.7 g of ammonium metavanadate and 373.1 g of antimony(III) oxide were added to 8,330 g of water, and the resultant mixture was heated to about 90° C. for 2.5 hours under atmospheric pressure while stirring, to obtain a solution, and the obtained solution was cooled to about 70° C., to thereby obtain aqueous mixture A-4.

Preparation of Tungsten-containing Aqueous Solution C-2

Commercially available aqueous ammonium metatungstate solution (trade name: MW-2; manufactured and sold by Nippon Inorganic Colour & Chemical Co., Ltd., Japan) (concentration in terms of $WO_3$:50% by weight) was used as tungsten-containing aqueous solution C-2.

Preparation of an Oxide Catalyst

An oxide catalyst comprising a silica carrier having supported thereon an oxide (silica carrier content: 41.3% by weight in terms of $SiO_2$, based on the total weight of the oxide and the silica carrier) in which the oxide is represented by the formula:

$Mo_1V_{0.32}Nb_{0.07}Sb_{0.23}Ti_{0.85}W_{0.05}O_n$, was prepared as follows.

To the above-mentioned aqueous mixture A-4 was added 7,843.1 g of a silica sol (having an $SiO_2$ content of 30.6% by weight) and then added 579.8 g of an aqueous hydrogen peroxide (having an $H_2O_2$ content of 15% by weight). The resultant mixture was subjected to oxidation treatment wherein the mixture was stirred at 50° C. for 1 hour, to thereby obtain an oxidized mixture. In the above oxidation treatment, the [$H_2O_2$:Sb] molar ratio was 1.

To the obtained oxidized mixture was added 1,197.3 g of the niobium-containing aqueous solution B-2 prepared in Example 4, the aqueous mixture C-1 as prepared in Example 4 and 257.8 g of the above-mentioned tungsten-containing aqueous solution C-2 to thereby obtain a slurry of a raw material mixture. The obtained slurry was easy to handle, because of the excellent dispersibility of the particles in the obtained slurry.

The obtained slurry was subjected to spray drying using a centrifugation type spray-drying apparatus under conditions wherein the inlet and outlet temperatures of the apparatus were 210° C. and 120° C., respectively, to thereby obtain a dried, microspherical particulate catalyst precursor.

480 g of the obtained dried catalyst precursor was charged into a SUS rotary kiln (inner diameter: 3 inch), and then calcined at 660° C. for 2 hours under a stream of nitrogen gas at a flow rate of 1,800 Ncc/min, to thereby obtain an oxide catalyst comprising an oxide of the above formula.

With respect to the oxygen concentration of the nitrogen gas used for the calcination, measurement was done by means of a trace oxygen analyzer (type 306WA; manufactured and sold by Teledyne Analytical Instruments, U.S.A.). As a result, it was found that the oxygen concentration of the nitrogen gas was 1 ppm.

Ammoxidation of Propane

An ammoxidation of propane was performed in the presence of the oxide catalyst obtained above under the same conditions as in Example 1. The results of the ammoxidation are shown in Table 1.

EXAMPLE 7

Preparation of Aqueous Mixture A-5

250 g of ammonium heptamolybdate, 49.7 g of ammonium metavanadate and 47.5 g of antimony(III) oxide were added to 1,000 g of water, and the resultant mixture was refluxed at 100° C. for 2 hours under atmospheric pressure, to obtain a solution, and the obtained solution was cooled to about 50° C., to thereby obtain aqueous mixture A-5.

Preparation of Niobium-containing Aqueous Solution B-3

To 120 g of water were added 17.3 g of niobic acid ($Nb_2O_5$ content: 76% by weight) and 33.7 g of oxalic acid dihydrate, and the resultant mixture was stirred at 60° C., to obtain a solution, and the obtained solution was cooled to about 30° C., to thereby obtain niobium-containing aqueous solution B-3. The oxalic acid/Nb molar ratio of the aqueous solution B-3 was 2.7.

Preparation of Aqueous Mixture C-3

7.2 g of aluminum oxide (Product code: 012-01965; manufactured and sold by Wako Pure Chemical Industries, Ltd., Japan) was added to 50 g of water and the resultant mixture was vigorously stirred for 1 hour so that the aluminum oxide was suspended in water, thereby obtaining aqueous mixture C-3.

The above-mentioned aluminum oxide was analyzed by X-ray diffractometry (XRD) using an X-ray diffractometer RAD-IIIA (manufactured and sold by Rigaku Corporation, Japan). As a result, it was found that the aluminum oxide was α-alumina having a high crystallinity.

TABLE 1

|  | Compostion | Crystal structure of the Z oxide | Type of reactor | Conversion of propane (%) | Selectivity for acrylonitrile (%) |
|---|---|---|---|---|---|
| Ex. 1 | $Mo_1V_{0.32}Nb_{0.07}Sb_{0.23}Ti_{0.85}O_n/SiO_2$(43.2 wt %) | Rutile structure | Fluidized-bed reactor | 50.8 | 64.2 |
| Comp. Ex. 1 | $Mo_1V_{0.32}Nb_{0.07}Sb_{0.23}O_n/SiO_2$(50.0 wt %) | — | Fluidized-bed reactor | 50.3 | 61.8 |
| Comp. Ex. 2 | $Mo_1V_{0.32}Nb_{0.07}Sb_{0.23}Ti_{0.85}O_n/SiO_2$(43.2 wt %) | Anatase structure | Fluidized-bed reactor | 21.5 | 9.2 |
| Comp. EX. 3 | [$Mo_1V_{0.32}Nb_{0.07}Sb_{0.23}O_n/SiO_2$(50.0 wt %)] + $TiO_2$ (two compounds are only physically mixed) | — | Fixed-bed reactor | 49.2 | 53.7 |
| Ex. 2 | $Mo_1V_{0.32}Nb_{0.07}Sb_{0.23}Ti_{0.55}Sn_{0.3}O_n/SiO_2$(41.4 wt %) | Ti: Rutile structure Sn: Rutile structure | Fluidized-bed reactor | 50.1 | 63.3 |
| Ex. 3 | $Mo_1V_{0.32}Nb_{0.07}Sb_{0.23}Ti_{0.85}Sn_{0.3}O_n/SiO_2$(39.6 wt %) | Ti: Rutile structure Sn: Rutile structure | Fluidized-bed reactor | 51.0 | 63.6 |
| Ex. 4 | $Mo_1V_{0.32}Nb_{0.07}Sb_{0.23}Ti_{0.85}O_n/SiO_2$(43.2 wt %) | Rutile structure | Fluidized-bed reactor | 50.0 | 64.5 |
| Ex. 5 | $Mo_1V_{0.32}Nb_{0.07}Sb_{0.23}Ti_{0.55}O_n/SiO_2$(45.4 wt %) | Rutile structure | Fluidized-bed reactor | 50.4 | 65.0 |
| Ex. 6 | $Mo_1V_{0.32}Nb_{0.07}Sb_{0.23}Ti_{0.85}W_{0.05}O_n/SiO_2$(41.3 wt %) | Rutile structure | Fluidized-bed reactor | 51.7 | 63.8 |

Notes:
1) The reaction conditions for the catalytic ammoxidation of propane in the gaseous phase are as follows.
Reactor: fluidized-bed reactor (25 mm φ) or fixed-bed reactor (10 mm φ);
Reaction temperature: 440° C.;
Reaction pressure: atmospheric pressure (1 atm);
Contact time: 3.0 sec · g/cc;
Composition of the raw material mixture gas: [propane:ammonia:molecular oxygen:helium] molar ratio = 1:0.6:1.5:5.6.
2) The number in the parentheses is the amount (% by weight) of the silica carrier in terms of $SiO_2$, based on the total weight of the oxide and the silica carrier in terms of $SiO_2$.

Preparation of an Oxide Catalyst

An oxide catalyst comprising a silica carrier having supported thereon an oxide (silica carrier content: 40% by weight in terms of $SiO_2$, based on the total weight of the oxide and the silica carrier), in which the oxide is represented by the formula:

$$Mo_1V_{0.3}Nb_{0.07}Sb_{0.23}Al_{0.1}O_n,$$

was prepared as follows.

To the above-mentioned aqueous mixture A-5 was added 689 g of a silica sol (having an $SiO_2$ content of 30% by weight) and stirred for 1 hour, thereby obtaining a mixture. To the obtained mixture was added 221 g of an aqueous hydrogen peroxide (having an $H_2O_2$ content of 5% by weight). The resultant mixture was subjected to oxidation treatment wherein the mixture was stirred at 50° C. for 1 hour, to thereby obtain an oxidized mixture. In the above oxidation treatment, the [$H_2O_2$:Sb] molar ratio was 1.

To the obtained oxidized mixture was added the above-prepared niobium-containing aqueous solution B-3 and aqueous mixture C-3, and the resultant mixture was heated at 50° C. for 30 minutes under atmospheric pressure, to thereby obtain a slurry of a raw material mixture. The obtained slurry was easy to handle, because of the excellent dispersibility of the particles in the obtained slurry.

The obtained slurry was subjected to spray drying using a centrifugation type spray-drying apparatus under conditions wherein the inlet and outlet temperatures of the apparatus were 230° C. and 120° C., respectively, to thereby obtain a dried, microspherical particulate catalyst precursor.

100 g of the obtained dried catalyst precursor was charged into a quartz container (inner diameter: 3 inch), and then calcined in a kiln at 640° C. for 2 hours under a stream of nitrogen gas at a flow rate of 600 Ncc/min while rotating the quartz container, to thereby obtain an oxide catalyst comprising an oxide of the above formula.

With respect to the oxygen concentration of the nitrogen gas used for the calcination, measurement was done by means of a trace oxygen analyzer (type 306WA; manufactured and sold by Teledyne Analytical Instruments, U.S.A.). As a result, it was found that the oxygen concentration of the nitrogen gas was 1 ppm.

Ammoxidation of Propane

Using the catalyst obtained above, an ammoxidation of propane was performed as follows.

0.35 g (W=0.35 g) of the obtained catalyst was charged into a fixed-bed reaction tube having an inner diameter of 4 mm. In the reaction tube containing the catalyst, an ammoxidation of propane was performed under conditions wherein the temperature (T) was 420° C., the pressure (P) was atmospheric (i.e., 1 atm) and the contact time between the catalyst and a gaseous feed-stock mixture (i.e., a gaseous mixture of propane, ammonia, molecular oxygen and helium, wherein the [propane:ammonia:molecular oxygen: helium] molar ratio was 1:0.7:1.7:5.3) was 2.1 g·sec/cc.

The results of the above ammoxidation are shown in Table 2.

EXAMPLE 8

Preparation of an Oxide Catalyst

An oxide catalyst comprising a silica carrier having supported thereon an oxide (silica carrier content: 40% by weight in terms of $SiO_2$, based on the total weight of the oxide and the silica carrier), in which the oxide is represented by the formula:

$$Mo_1V_{0.3}Nb_{0.07}Sb_{0.23}Al_{0.05}O_n,$$

was prepared in substantially the same manner as in Example 7, except that 3.6 g of aluminum oxide was used in the preparation of the aqueous mixture C-3 and that 681 g of the silica sol was used.

Ammoxidation of Propane

An ammoxidation of propane was performed in the presence of the oxide catalyst obtained above under the same conditions as in Example 7. The results of the ammoxidation are shown in Table 2.

EXAMPLE 9

Preparation of an Oxide Catalyst

An oxide catalyst comprising a silica carrier having supported thereon an oxide (silica carrier content: 40% by weight in terms of $SiO_2$, based on the total weight of the oxide and the silica carrier), in which the oxide is represented by the formula:

$$Mo_1V_{0.3}Nb_{0.07}Sb_{0.23}Al_{0.3}O_n,$$

was prepared in substantially the same manner as in Example 7, except that 21.6 g of aluminum oxide was used in the preparation of the aqueous mixture C-3 and that 721 g of the silica sol was used.

Ammoxidation of Propane

An ammoxidation of propane was performed in the presence of the oxide catalyst obtained above under the same conditions as in Example 7. The results of the ammoxidation are shown in Table 2.

COMPARATIVE EXAMPLE 4

Preparation of an Oxide Catalyst

An oxide catalyst comprising a silica carrier having supported thereon an oxide (silica carrier content: 40% by weight in terms of $SiO_2$, based on the total weight of the oxide and the silica carrier), in which the oxide is represented by the formula:

$$Mo_1V_{0.3}Nb_{0.07}Sb_{0.23}O_n,$$

was prepared in substantially the same manner as in Example 7, except that the use of the aqueous mixture C-3 was omitted and that 673 g of the silica sol was used.

Ammoxidation of Propane

An ammoxidation of propane was performed in the presence of the oxide catalyst obtained above under the same conditions as in Example 7. The results of the ammoxidation are shown in Table 2.

COMPARATIVE EXAMPLE 5

Preparation of an Oxide Catalyst

An oxide catalyst comprising a silica carrier having supported thereon an oxide (silica carrier content: 40% by weight in terms of $SiO_2$, based on the total weight of the oxide and the silica carrier), in which the oxide is represented by the formula:

$Mo_1V_{0.3}Nb_{0.07}Sb_{0.23}Al_{0.6}O_n$, was prepared in substantially the same manner as in Example 7, except that 43.3 g of aluminum oxide was used in the preparation of the aqueous mixture C-3 and that 770 g of the silica sol was used.

Ammoxidation of Propane

An ammoxidation of propane was performed in the presence of the oxide catalyst obtained above under the same conditions as in Example 7. The results of the ammoxidation are shown in Table 2.

Preparation of Compound Oxide $Al_1Sb_1O_3$ 200 g of aluminum nitrate ($Al(NO_3)_3 \cdot 9H_2O$) was dissolved in 1,500 g of water, thereby obtaining an aluminum nitrate solution. To the obtained aluminum nitrate solution was added 77.5 g of antimony(III) oxide, and the resultant mixture was vigorously stirred for 2 hours at 80° C., to thereby obtain an aqueous mixture.

The obtained mixture was subjected to spray drying using a centrifugation type spray-drying apparatus under conditions wherein the inlet and outlet temperatures of the apparatus were 230° C. and 120° C., respectively, to thereby obtain a dried, microspherical powder.

100 g of the obtained dried powder was calcined at 900° C. for 2 hours in an atmosphere of air, to thereby obtain a compound oxide.

The obtained compound oxide was analyzed by XRD using an X-ray diffractometer RAD-IIIA (manufactured and sold by Rigaku Corporation, Japan). As a result, compound oxide $AlSbO_4$ having a rutile structure and α-type antimony (v) antimony(III) oxide ($Sb_2O_4$) were detected. These results show the fact that although the molar amounts of aluminum

TABLE 2

| | Composition | Conversion of propane (%) | Selectivity for acrylonitrile (%) |
|---|---|---|---|
| Ex. 7 | $Mo_1V_{0.3}Sb_{0.23}Nb_{0.07}Al_{0.1}O_n/SiO_2$(40.0 wt %) | 48.5 | 64.9 |
| Ex. 8 | $Mo_1V_{0.3}Sb_{0.23}Nb_{0.07}Al_{0.05}O_n/SiO_2$(40.0 wt %) | 48.4 | 64.8 |
| Ex. 9 | $Mo_1V_{0.3}Sb_{0.23}Nb_{0.07}Al_{0.3}O_n/SiO_2$(40.0 wt %) | 48.2 | 64.5 |
| Comp. Ex. 4 | $Mo_1V_{0.3}Sb_{0.23}Nb_{0.07}O_n/SiO_2$(40.0 wt %) | 48.5 | 63.9 |
| Comp. Ex. 5 | $Mo_1V_{0.3}Sb_{0.23}Nb_{0.07}Al_{0.6}O_n/SiO_2$(40.0 wt %) | 47.9 | 61.0 |

Notes:
1) The reaction conditions for the catalytic ammoxidation of propane in the gaseous phase are as follows.
Reactor: fixed-bed reactor (4 mm φ);
Reaction temperature: 420° C.;
Reaction pressure: atmospheric pressure (1 atm);
Contact time: 2.1 sec · g/cc;
Composition of the raw material mixture gas: [propane:ammonia:molecular oxygen:helium] molar ratio = 1:0.7:1.7:5.3.
2) The number in the parentheses is the amount (% by weight) of the silica carrier in terms of $SiO_2$, based on the total weight of the oxide and the silica carrier in terms of $SiO_2$.

EXAMPLE 10

Preparation of Aqueous Mixture A-6

250 g of ammonium heptamolybdate, 49.7 g of ammonium metavanadate and 41.3 g of antimony(III) oxide were added to 1,000 g of water, and the resultant mixture was refluxed at 100° C. for 2 hours under atmospheric pressure, to obtain a solution, and the obtained solution was cooled to about 50° C., to thereby obtain aqueous mixture A-6.

Preparation of Niobium-containing Aqueous Solution B-4

To 120 g of water were added 12.4 g of niobic acid ($Nb_2O_5$ content: 76% by weight) and 24.1 g of oxalic acid dehydrate, and the resultant mixture was stirred at 60° C., to obtain a solution, and the obtained solution was cooled to about 30° C., to thereby obtain niobium-containing aqueous solution B-4. The oxalic acid/Nb molar ratio of the aqueous solution B-4 was 2.7.

and antimony in the raw materials were the same, the α-type $Sb_2O_4$ which contains no aluminum was detected together with compound oxide $AlSbO_4$ in which the molar amounts of aluminum and antimony in the raw materials are the same. From this fact, it was apparent that the above-obtained compound oxide contained a non-crystalline aluminum compound (unidentified). Therefore, it was concluded that the obtained compound oxide was actually a mixture of the compound oxide $AlSbO_4$, the α-type $Sb_2O_4$ and a non-crystalline aluminum compound. Hereinafter, the obtained compound oxide (mixture) is referred to as the "compound oxide $Al_1Sb_1O_3$".

The content of the compound oxide $AlSbO_4$ in the compound oxide $Al_1Sb_1O_3$, which content was determined from the X-ray diffraction pattern obtained by the above-mentioned XRD (i.e., the ratio of the total area of the peaks ascribed to the compound oxide $AlSbO_4$ to the total area of the peaks observed at a diffraction angle (2θ) within the range of from 10 to 60° in the X-ray diffraction pattern obtained by the above-mentioned XRD), was approximately 70%.

Preparation of Aqueous Mixture C-4

25.1 g of the compound oxide $Al_1Sb_1O_3$ was added to 100 g of water, and the resultant mixture was stirred using a homogenizer (8,000 rpm) for 10 minutes to thereby obtain aqueous mixture C-4.

Preparation of an Oxide Catalyst

An oxide catalyst comprising a silica carrier having supported thereon an oxide (silica carrier content: 45% by weight in terms of $SiO_2$, based on the total weight of the oxide and the silica carrier), in which the oxide is represented by the formula:

$Mo_1V_{0.3}Nb_{0.05}Sb_{0.29}Al_{0.09}O_n$, was prepared as follows.

To the above-mentioned aqueous mixture A-6 was added 868 g of a silica sol (having an $SiO_2$ content of 30% by weight) and stirred for 1 hour, thereby obtaining a mixture. To the obtained mixture was added 193 g of an aqueous hydrogen peroxide (having an $H_2O_2$ content of 5% by weight). The resultant mixture was subjected to oxidation treatment wherein the mixture was stirred at 50° C. for 1 hour, to thereby obtain an oxidized mixture. In the above oxidation treatment, the [$H_2O_2$:Sb] molar ratio was 1.

To the obtained oxidized mixture were added the above-prepared niobium-containing aqueous solution B-4 and aqueous mixture C-4, and the resultant mixture was stirred at 50° C. for 30 minutes under atmospheric pressure, to thereby obtain a slurry of a raw material mixture. The obtained slurry was easy to handle, because of the excellent dispersibility of the particles in the obtained slurry.

The obtained slurry was subjected to spray drying using a centrifugation type spray-drying apparatus under conditions wherein the inlet and outlet temperatures of the apparatus were 230° C. and 120° C., respectively, to thereby obtain a dried, microspherical particulate catalyst precursor.

100 g of the obtained dried catalyst precursor was charged into a quartz container (inner diameter: 3 inch), and then calcined in a kiln at 630° C. for 2 hours under a stream of nitrogen gas at a flow rate of 600 Ncc/min while rotating the quartz container, to thereby obtain an oxide catalyst comprising an oxide of the above formula.

With respect to the oxygen concentration of the nitrogen gas used for the calcination, measurement was done by means of a trace oxygen analyzer (type 306WA; manufactured and sold by Teledyne Analytical Instruments, U.S.A.). As a result, it was found that the oxygen concentration of the nitrogen gas was 1 ppm.

Ammoxidation of Propane

Using the catalyst obtained above, an ammoxidation of propane was performed as follows.

0.35 g (W=0.35 g) of the obtained catalyst was charged into a fixed-bed reaction tube having an inner diameter of 4 mm. In the reaction tube containing the catalyst, an ammoxidation of propane was performed under conditions wherein the temperature (T) was 420° C., the pressure (P) was atmospheric (i.e., 1 atm) and the contact time between the catalyst and a gaseous feed-stock mixture (i.e., a gaseous mixture of propane, ammonia, molecular oxygen and helium, wherein the [propane:ammonia:molecular oxygen:helium] molar ratio was 1:0.7:1.7:5.3) was 2.3 g·sec/cc.

The results of the above ammoxidation are shown in Table 3.

COMPARATIVE EXAMPLE 6

Preparation of an Oxide Catalyst

An oxide catalyst comprising a silica carrier having supported thereon an oxide (silica carrier content: 45% by weight in terms of $SiO_2$, based on the total weight of the oxide and the silica carrier), in which the oxide is represented by the formula:

$Mo_1V_{0.30}Nb_{0.05}Sb_{0.20}O_n$, was prepared in substantially the same manner as in Example 10, except that the use of the aqueous mixture C-4 was omitted and that 799 g of the silica sol was used.

Ammoxidation of Propane

An ammoxidation of propane was performed in the presence of the oxide catalyst obtained above under the same conditions as in Example 10. The results of the ammoxidation are shown in Table 3.

COMPARATIVE EXAMPLE 7

Preparation of Oxide Catalyst 0.334 g of the oxide catalyst prepared in COMPARATIVE EXAMPLE 6 and 0.016 g of the compound oxide $Al_1Sb_1O_3$ obtained in Example 10 were charged into a 5 cc glass vessel and the vessel was vigorously shaken for 5 minutes to thereby obtain a mixture. The obtained mixture was used as an oxide catalyst. The atomic ratio of aluminum (contained in the compound oxide $Al_1Sb_1O_3$) to molybdenum (contained in the oxide catalyst prepared in COMPARATIVE EXAMPLE 6) was 0.09.

Ammoxidation of Propane

An ammoxidation of propane was performed in the presence of the oxide catalyst obtained above under the same conditions as in Example 10. The results of the ammoxidation are shown in Table 3.

EXAMPLE 11

Preparation of Compound Oxide $Al_{1.2}Sb_1O_{3.3}$

A compound oxide was prepared in substantially the same manner as in the item <Preparation of compound oxide $Al_1Sb_1O_3$> of Example 10, except that 240 g of aluminum nitrate was used.

The obtained compound oxide was analyzed by XRD using an X-ray diffractometer RAD-IIIA (manufactured and sold by Rigaku Corporation, Japan). As a result, compound oxide $AlSbO_4$ having a rutile structure and α-type antimony (v) antimony(III) oxide ($Sb_2O_4$) were detected. These results show the fact that although the molar amount of aluminum in the raw materials was larger than that of antimony in the raw materials, the α-type $Sb_2O_4$ which contains no aluminum was detected together with compound oxide $AlSbO_4$ in which the molar amounts of aluminum and antimony in the raw materials are the same. From this fact, it was apparent that the above-obtained compound oxide contains a non-crystalline aluminum compound (unidentified). Therefore, it was concluded that the obtained compound oxide was actually a mixture of the compound oxide $AlSbO_4$, the α-type $Sb_2O_4$ and a non-crystalline aluminum compound. Hereinafter, the obtained compound oxide (mixture) is referred to as the "compound oxide $Al_{1.2}Sb_1O_{3.3}$".

The content of compound oxide $AlSbO_4$ in the compound oxide $Al_{1.2}Sb_1O_{3.3}$, which content was determined from the X-ray diffraction pattern obtained by the above-mentioned XRD (i.e., the ratio of the total area of the peaks ascribed to the compound oxide $AlSbO_4$ to the total area of the peaks observed at a diffraction angle (2θ) within the range of from 10 to 60° in the X-ray diffraction pattern obtained by the above-mentioned XRD), was approximately 80%.

Preparation of an Oxide Catalyst

An oxide catalyst comprising a silica carrier having supported thereon an oxide (silica carrier content: 45% by weight in terms of $SiO_2$, based on the total weight of the oxide and the silica carrier), in which the oxide is represented by the formula:

$$Mo_1V_{0.30}Nb_{0.05}Sb_{0.29}Al_{0.11}O_n,$$

was prepared in substantially the same manner as in Example 10, except that 871 g of the silica sol was used and that 26.4 g of $Al_{1.2}Sb_1O_{3.3}$ was used instead of 25.1 g of $Al_1Sb_1O_3$.

Ammoxidation of Propane

An ammoxidation of propane was performed in the presence of the oxide catalyst obtained above under the same conditions as in Example 10. The results of the ammoxidation are shown in Table 3.

EXAMPLE 12

Preparation of Compound Oxide $Fe_1Sb_1O_3$ 200 g of iron nitrate ($Fe(NO_3)_3 \cdot 9H_2O$) was dissolved in 1,500 g of water, thereby obtaining an iron nitrate solution. To the obtained iron nitrate solution was added 72 g of antimony(III) oxide, and the resultant mixture was vigorously stirred for 2 hours at 80° C., to thereby obtain an aqueous mixture.

The obtained mixture was subjected to spray drying using a centrifugation type spray-drying apparatus under conditions wherein the inlet and outlet temperatures of the apparatus were 230° C. and 120° C., respectively, to thereby obtain a dried, microspherical powder.

100 g of the obtained dried powder was calcined at 900° C. for 2 hours in an atmosphere of air, to thereby obtain a compound oxide.

The obtained compound oxide was analyzed by XRD using an X-ray diffractometer RAD-IIIA (manufactured and sold by Rigaku Corporation, Japan). As a result, compound oxide $FeSbO_4$ having a rutile structure was detected. The obtained compound oxide was considered to contain, in addition to compound oxide $FeSbO_4$, a small amount of a non-crystalline iron compound (unidentified) and a small amount of a non-crystalline antimony compound (unidentified). Therefore, it was concluded that the obtained compound oxide was actually a mixture of the compound oxide $FeSbO_4$, a non-crystalline iron compound (unidentified) and a non-crystalline antimony compound. Hereinafter, the obtained compound oxide (mixture) is referred to as the "compound oxide $Fe_1Sb_1O_3$".

The content of the compound oxide $FeSbO_4$ in the compound oxide $Fe_1Sb_1O_3$, which content was determined from the X-ray diffraction pattern obtained by the above-mentioned XRD (i.e., the ratio of the total area of the peaks ascribed to the compound oxide $FeSbO_4$ to the total area of the peaks observed at a diffraction angle (2θ) within the range of from 10 to 60° in the X-ray diffraction pattern obtained by the above-mentioned XRD), was approximately 100%.

Preparation of an Oxide Catalyst

An oxide catalyst comprising a silica carrier having supported thereon an oxide (silica carrier content: 45% by weight in terms of $SiO_2$, based on the total weight of the oxide and the silica carrier), in which the oxide is represented by the formula:

$$Mo_1V_{0.30}Nb_{0.05}Sb_{0.25}Fe_{0.05}O_n,$$

was prepared in substantially the same manner as in Example 10, except that 843 g of the silica sol was used and that 16.0 g of $Fe_1Sb_1O_3$ was used instead of 25.1 g of $Al_1Sb_1O_3$.

Ammoxidation of Propane

An ammoxidation of propane was performed in the presence of the oxide catalyst obtained above under the same conditions as in Example 10. The results of the ammoxidation are shown in Table 3.

COMPARATIVE EXAMPLE 8

Preparation of Oxide Catalyst 0.340 g of the oxide catalyst prepared in COMPARATIVE EXAMPLE 6 and 0.010 g of the compound oxide $Fe_1Sb_1O_3$ obtained in Example 11 were charged into a 5 cc glass vessel and the vessel was vigorously shaken for 5 minutes to thereby obtain a mixture. The obtained mixture was used as an oxide catalyst. The atomic ratio of iron (contained in the compound oxide $Fe_1Sb_1O_3$) to molybdenum (contained in the oxide catalyst prepared in COMPARATIVE EXAMPLE 6) was 0.05.

Ammoxidation of Propane

An ammoxidation of propane was performed in the presence of the oxide catalyst obtained above under the same conditions as in Example 10. The results of the ammoxidation are shown in Table 3.

TABLE 3

|  | Composition | Crystal structure of the Z oxide | Conversion of propane (%) | Selectivity for acrylonitrile (%) |
| --- | --- | --- | --- | --- |
| Ex. 10 | $Mo_1V_{0.30}Sb_{0.29}Nb_{0.05}Al_{0.09}O_n/SiO_2$(45.0 wt %) | Rutile structure ($AlSbO_4$) | 48.4 | 64.0 |

TABLE 3-continued

| | Composition | Crystal structure of the Z oxide | Conversion of propane (%) | Selectivity for acrylonitrile (%) |
|---|---|---|---|---|
| Comp. Ex. 6 | $Mo_1V_{0.30}Sb_{0.20}Nb_{0.05}O_n/SiO_2$(45.0 wt %) | — | 48.6 | 62.8 |
| Comp. Ex. 7 | [$Mo_1V_{0.30}Sb_{0.20}Nb_{0.05}O_n/SiO_2$(45.0 wt %)] + $Al_1Sb_1O_n$ (Two compounds are only physically mixed; Mo:Al atomic ratio = 1:0.09) | — | 46.8 | 64.8 |
| Ex. 11 | $Mo_1V_{0.30}Sb_{0.29}Nb_{0.05}Al_{0.11}O_n/SiO_2$(45.0 wt %) | Rutile structure ($AlSbO_4$) | 48.5 | 65.0 |
| Ex. 12 | $Mo_1V_{0.30}Sb_{0.25}Nb_{0.05}Fe_{0.05}O_n/SiO_2$(45.0 wt %) | Rutile structure ($FeSbO_4$) | 48.4 | 64.4 |
| Comp. Ex. 8 | [$Mo_1V_{0.30}Sb_{0.20}Nb_{0.05}O_n/SiO_2$(45.0 wt %)] + $Fe_1Sb_1O_n$ (Two compounds are only physically mixed; Mo:Fe atomic ratio = 1:0.05) | — | 47.9 | 62.4 |

Notes:
1) The reaction conditions for the catalytic ammoxidation of propane in the gaseous phase are as follows.
Reactor: fixed-bed reactor (4 mm φ);
Reaction temperature: 420° C.;
Reaction pressure: atmospheric pressure (1 atm);
Contact time: 2.3 sec · g/cc;
Composition of the raw material mixture gas: [propane:ammonia:molecular oxygen:helium] molar ratio = 1:0.7:1.7:5.3.
2) The number in the parentheses is the amount (% by weight) of the silica carrier in terms of $SiO_2$, based on the total weight of the oxide and the silica carrier in terms of $SiO_2$.

EXAMPLE 13

Preparation of an Oxide Catalyst

An oxide catalyst consisting of the oxide represented by the formula:

$$Mo_1V_{0.30}Nb_{0.05}Sb_{0.29}Al_{0.09}O_n,$$

was prepared in substantially the same manner as in Example 10, except that the use of the silica sol was omitted.

Oxidation of Propane

Using the catalyst obtained above, an oxidation of propane was performed as follows.

0.35 g (W=0.35 g) of the obtained catalyst was charged into a fixed-bed reaction tube having an inner diameter of 4 mm. In the reaction tube containing the catalyst, an ammoxidation of propane was performed under conditions wherein the temperature (T) was 380° C., the pressure (P) was atmospheric (i.e., 1 atm) and the contact time between the catalyst and a gaseous feed-stock mixture (i.e., a gaseous mixture of propane, ammonia, molecular oxygen and helium, wherein the [propane:molecular oxygen:steam:helium] molar ratio was 1:3:14:10) was 2.0 g·sec/cc.

The results of the above oxidation are shown in Table 4.

COMPARATIVE EXAMPLE 9

Preparation of an Oxide Catalyst

An oxide consisting of the oxide represented by the formula:

$$Mo_1V_{0.30}Nb_{0.05}Sb_{0.20}O_n,$$

was prepared in substantially the same manner as in COMPARATIVE EXAMPLE 6, except that the use of the silica sol was omitted.

Oxidation of Propane

An oxidation of propane was performed in the presence of the oxide catalyst obtained above under the same conditions as in Example 13. The results of the oxidation are shown in Table 4.

EXAMPLE 14

Oxidation of Propane

An oxidation of propane was performed in the presence of the oxide catalyst obtained in Example 1 under the same conditions as in Example 13. The results of the oxidation are shown in Table 4.

EXAMPLE 15

Oxidation of Propane

An oxidation of propane was performed in the presence of the oxide catalyst obtained in Example 2 under the same conditions as in Example 13. The results of the oxidation are shown in Table 4.

EXAMPLE 16

Oxidation of Propane

An oxidation of propane was performed in the presence of the oxide catalyst obtained in Example 4 under the same conditions as in Example 13. The results of the oxidation are shown in Table 4.

COMPARATIVE EXAMPLE 10

Oxidation of Propane

An oxidation of propane was performed in the presence of the oxide catalyst obtained in Comparative Example 1 under the same conditions as in Example 13. The results of the oxidation are shown in Table 4.

ratus were 210° C. and 120° C., respectively, to thereby obtain a dried, microspherical particulate catalyst precursor.

TABLE 4

|  | Composition | Crystal structure of the Z oxide | Conversion of propane (%) | Selectivity for acrylic acid (%) |
| --- | --- | --- | --- | --- |
| Ex. 13 | $Mo_1V_{0.30}Sb_{0.29}Nb_{0.05}Al_{0.09}O_n$ | Rutile structure (AlSbO$_4$) | 63.5 | 51.0 |
| Comp. Ex. 9 | $Mo_1V_{0.30}Sb_{0.20}Nb_{0.05}O_n$ | — | 63.2 | 47.8 |
| Ex. 14 | $Mo_1V_{0.32}Nb_{0.07}Sb_{0.23}Ti_{0.85}O_n/SiO_2$(43.2 wt %) | Rutile structure | 64.6 | 52.5 |
| Ex. 15 | $Mo_1V_{0.32}Nb_{0.07}Sb_{0.23}Ti_{0.55}Sn_{0.3}O_n/SiO_2$(41.4 wt %) | Rutile structure | 62.8 | 51.2 |
| Ex. 16 | $Mo_1V_{0.32}Nb_{0.07}Sb_{0.23}Ti_{0.85}O_n/SiO_2$(43.2 wt %) | Rutile structure | 63.9 | 52.2 |
| Comp. Ex. 10 | $Mo_1V_{0.32}Nb_{0.07}Sb_{0.23}O_n/SiO_2$(50.0 wt %) | — | 62.3 | 46.7 |

Notes:
1) The reaction conditions for the catalytic oxidation of propane in the gaseous phase are as follows.
Reactor: fixed-bed reactor (4 mm $\phi$);
Reaction temperature: 380° C.;
Reaction pressure: atmospheric pressure (1 atm);
Contact time: 2.0 sec · g/cc;
Composition of the raw material mixture gas: [propane:molecular oxygen:steam:helium] molar ratio = 1:3:14:10.
2) The number in the parentheses is the amount (% by weight) of the silica carrier in terms of SiO$_2$, based on the total weight of the oxide and the silica carrier in terms of SiO$_2$.

EXAMPLE 17

Preparation of Aqueous Mixture A-7

400.3 g of ammonium heptamolybdate, 100.8 g of ammonium metavanadate and 93.7 g of telluric acid (H$_6$TeO$_6$) were added to 2,000 g of water, and the resultant mixture was heated to about 90° C. for 1 hour under atmospheric pressure while stirring, to obtain a solution, and the obtained solution was cooled to about 70° C., to thereby obtain aqueous mixture A-7.

Preparation of Aqueous Mixture C-5

90.5 g of rutile titanium oxide (in the form of quasi-spherical particles having an average particle diameter of 0.25 μm) was added to 1,000 g of water, and the resultant mixture was stirred, to thereby obtain aqueous mixture C-5.

Preparation of an Oxide Catalyst

An oxide catalyst comprising a silica carrier having supported thereon an oxide (silica carrier content: 45.9% by weight in terms of SiO$_2$, based on the total weight of the oxide and the silica carrier), in which the oxide is represented by the formula:

$Mo_1V_{0.38}Nb_{0.08}Te_{0.18}Ti_{0.50}O_n$,

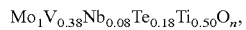

was prepared as follows.
To the above-mentioned aqueous mixture A-7 was added 1,634.0 g of a silica sol (having an SiO$_2$ content of 30.6% by weight), thereby obtaining a mixture.
To the obtained mixture was added 278.8 g of the niobium-containing aqueous solution B-2 obtained in Example 4 and the above-mentioned aqueous mixture C-5, to thereby obtain a slurry of a raw material mixture. The obtained slurry was easy to handle, because of the excellent dispersibility of the particles in the obtained slurry.
The obtained slurry was subjected to spray drying using a centrifugation type spray-drying apparatus under conditions wherein the inlet and outlet temperatures of the appa- 85 g of the obtained dried catalyst precursor was charged into a SUS rotary kiln (inner diameter: 1 inch), And then calcined at 600° C. for 2 hours under a stream of nitrogen gas at a flow rate of 150 Ncc/min, to thereby obtain an oxide catalyst comprising an oxide of the above formula.
With respect to the oxygen concentration of the nitrogen gas used for the calcination, measurement was done by means of a trace oxygen analyzer (type 306WA; manufactured and sold by Teledyne Analytical Instruments, U.S.A.). As a result, it was found that the oxygen concentration of the nitrogen gas was 1 ppm.

Ammoxidation of Propane

Using the catalyst obtained above, an ammoxidation of propane was performed as follows.
1.0 g (W=1.0 g) of the obtained catalyst was charged into a fixed-bed reaction tube having an inner diameter of 10 mm. In the reaction tube containing the catalyst, an ammoxidation of propane was performed under conditions wherein the temperature (T) was 430° C., the pressure (P) was atmospheric (i.e., 1 atm) and the contact time between the catalyst and a gaseous feed-stock mixture (i.e., a gaseous mixture of propane, ammonia, molecular oxygen and helium, wherein the [propane:ammonia:molecular oxygen:helium] molar ratio was 1:0.7:1.6:5.5) was 2.0 g·sec/cc.
The results of the above ammoxidation are shown in Table 5.

COMPARATIVE EXAMPLE 11

Preparation of an Oxide Catalyst

An oxide catalyst comprising a silica carrier having supported thereon an oxide (silica carrier content: 50% by weight in terms of SiO$_2$, based on the total weight of the oxide and the silica carrier), in which the oxide is represented by the formula:

$Mo_1V_{0.38}Nb_{0.08}Te_{0.18}O_n$,

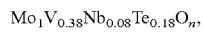

was prepared in substantially the same manner as in Example 17, except that the use of the aqueous mixture C-5 was omitted.

Ammoxidation of Propane

An ammoxidation of propane was performed in the presence of the oxide catalyst obtained above under the same conditions as in Example 17. The results of the ammoxidation are shown in Table 5.

TABLE 5

| | Composition | Crystal structure of the Z oxide | Conversion of propane (%) | Selectivity for acrylonitrile (%) |
|---|---|---|---|---|
| Ex. 17 | $Mo_1V_{0.38}Nb_{0.08}Te_{0.18}Ti_{0.50}O_n/SiO_2$(45.9 wt %) | Rutile structure | 49.4 | 64.5 |
| Comp. Ex. 11 | $Mo_1V_{0.38}Nb_{0.08}Te_{0.18}O_n/SiO_2$(50.0 wt %) | — | 47.8 | 60.5 |

Notes:
1) The reaction conditions for the catalytic ammoxidation of propane in the gaseous phase are as follows.
Reactor: fixed-bed reactor (10 mm φ);
Reaction temperature: 430° C.;
Reaction pressure: atmospheric pressure (1 atm);
Contact time: 2.0 sec · g/cc;
Composition of the raw material mixture gas: [propane:ammonia:molecular oxygen:helium] molar ratio = 1:0.7:1.6:5.5.
2) The number in the parentheses is the amount (% by weight) of the silica carrier in terms of $SiO_2$, based on the total weight of the oxide and the silica carrier in terms of $SiO_2$.

INDUSTRIAL APPLICABILITY

By the use of the oxide catalyst of the present invention for the catalytic oxidation or ammoxidation of propane or isobutane in the gaseous phase, it has become possible to improve the selectivity for the desired unsaturated carboxylic acids and unsaturated nitriles and to conduct an efficient production of the desired products. By virtue of these properties, the oxide catalyst of the present invention can be advantageously used in various industrial fields.

The invention claimed is:

1. An oxide catalyst for use in catalytic oxidation or ammoxidation of propane or isobutane in the gaseous phase, which comprises an oxide represented by the following formula (I):

$$Mo_1V_aNb_bX_cY_dZ_eQ_fO_n \quad (I)$$

wherein:
X is at least one element selected from the group consisting of tellurium and antimony;
Y is at least one element selected from the group consisting of aluminum and tungsten;
Z is at least one element selected from the group consisting of elements which individually form an oxide having a rutile structure and which are titanium, tin, germanium, lead, tantalum, ruthenium, rhenium, rhodium, iridium, platinum, molybdenum, vanadium, niobium, tellurium, antimony, aluminums and tungsten;
Q is at least one element selected from the group consisting of titanium, tin, germanium, lead, tantalum, ruthenium, rhenium, rhodium, iridium, platinum, chromium, manganese, technetium, osmium, iron, arsenic, cerium, cobalt, magnesium, nickel and zinc; and
a, b, c, d, e, f and n are, respectively, the atomic ratios of vanadium (V), niobium (Nb), X, Y, Z, Q and oxygen (O), relative to molybdenum (Mo),
wherein:
$0.1 \leq a \leq 1.0$,
$0.01 \leq b \leq 1.0$,
$0.01 \leq c \leq 1.0$,
$0 \leq d \leq 5$,
$0 \leq e \leq 3$,
$0 \leq f \leq 9$,
with the proviso that $0 < d+e \leq 3.5$, and
n is a number determined by and consistent with the valence requirements of the other elements present in the oxide of formula (I);
said oxide catalyst being produced by calcining a dried catalyst precursor, said precursor comprising:
(i) a molybdenum (Mo) compound which does not have a rutile structure;
(ii) a vanadium (V) compound which does not have a rutile structure;
(iii) a niobium (Nb) compound which does not have a rutile structure;
(iv) at least one X compound selected from the group consisting of compounds of elements defined as X in formula (I), wherein said X compound does not have a rutile structure;
(v) at least one compound selected from the group consisting of the following compounds (v-1) and (v-2):
(v-1) at least one Y compound selected from the group consisting of compounds of elements defined as Y in formula (I), wherein said Y compound does not have a rutile structure, and
(v-2) at least one Z oxide selected from the group consisting of oxides of elements defined as Z in formula (I), wherein said Z oxide has a rutile structure; and optionally
(vi) at least one Q compound selected from the group consisting of compounds of elements defined as Q in formula (I), wherein said Q compound does not have a rutile structure,
wherein said Mo compound, said V compound, said Nb compound, said X compound, said Y compound, said Z oxide and said Q compound are, respectively, used in amounts such that the atomic ratios of the Mo, V, Nb, X, Y, Z and Q in the catalyst obtained satisfy the atomic ratio requirements defined for formula (I).

2. The oxide catalyst according to claim 1, wherein X in formula (I) is antimony.

3. The oxide catalyst according to claim 1, wherein Y in formula (I) is aluminum and said compound (v-1) is aluminum oxide.

4. The oxide catalyst according to claim 1, wherein Z in formula (I) is at least one element selected from the group consisting of titanium and tin.

5. The oxide catalyst according to claim 1, which further comprises a silica carrier having supported thereon said oxide, wherein said silica carrier is present in an amount of from 20 to 60% by weight in terms of $SiO_2$, based on the total weight of said oxide and said silica carrier in terms of $SiO_2$.

6. The oxide catalyst according to claim 1, wherein said dried catalyst precursor further comprises a dicarboxylate value.

7. The oxide catalyst according to claim 1, wherein the calcination is performed in an inert gas atmosphere which is substantially free from molecular oxygen.

8. The oxide catalyst according to claim 1, wherein said dried catalyst precursor is produced by a method comprising the following steps (1) and (2):
(1) providing a solution or slurry of a raw material mixture in an aqueous medium, said raw material mixture comprising said compounds (i) to (vi); and
(2) drying said raw material mixture solution or slurry obtained in step (1), to thereby obtain said dried catalyst precursor.

9. The oxide catalyst according to claim 8, wherein, in step (1) of providing said raw material mixture solution or slurry, said niobium compound (iii) is used in the form of a niobium-containing aqueous solution comprising water having dissolved therein a dicarboxylic acid and said niobium compound (iii), wherein the molar ratio of said dicarboxylic acid to said niobium compound (iii) in terms of niobium is from 1 to 8.

10. The oxide catalyst according to claim 9, wherein said niobium-containing aqueous solution further comprises hydrogen peroxide, wherein the molar ratio of said hydrogen peroxide to said niobium compound (iii) in terms of niobium is from 0.5 to 10.

11. A process for producing acrylic acid or methacrylic acid, which comprises reacting propane or isobutane with molecular oxygen in the gaseous phase in the presence of the oxide catalyst of claim 1.

12. A process for producing acrylonitrile or methacrylonitrile, which comprises reacting propane or isobutane with ammonia and molecular oxygen in a gaseous phase in the presence of an oxide catalyst which comprises an oxide represented by the following formula (I):

$$Mo_1Y_aNb_bX_cY_dZ_eQ_fO_n \qquad (I)$$

wherein:
X is at least one element selected from the group consisting of tellurium and antimony;
Y is at least one element selected from the group consisting of aluminum and tungsten;
Z is at least one element selected from the group consisting of elements which individually form an oxide having a rutile structure and which are titanium, tin, germanium, lead, tantalum, ruthenium, rhenium, rhodium, iridium, platinum, molybdenum, vanadium, niobium, tellurium, antimony, aluminum and tungsten;

Q is at least one element selected from the group consisting of titanium, tin, germanium, lead, tantalum, ruthenium, rhenium, rhodium, iridium, platinum, chromium, manganese, technetium, osmium, iron, arsenic, cerium, cobalt, magnesium, nickel and zinc; and
a, b, c, d, e, f and n are, respectively, the atomic ratios of vanadium (V), niobium (Nb), X, Y, Z, Q and oxygen (O), relative to molybdenum (Mo),
wherein:
$0.1 \leq a \leq 1.0$,
$0.01 \leq b \leq 1.0$,
$0.01 \leq c \leq 1.0$,
$0 \leq d \leq 0.5$,
$0 \leq e \leq 3$,
$0 \leq f \leq 9$,
with the proviso that $0 < d+e \leq 3.5$, and
n is a number determined by and consistent with the valence requirements of the other elements present in the oxide of formula (I);
said oxide catalyst being produced by calcining a dried catalyst precursor, said precursor comprising:
(i) a molybdenum (Mo) compound which does not have a rutile structure;
(ii) a vanadium (V) compound which does not have a rutile structure;
(iii) a niobium (Nb) compound which does not have a rutile structure;
(iv) at least one X compound selected from the group consisting of compounds of elements defined as X in formula (I), wherein said X compound does not have a rutile structure;
(v) at least one compound selected from the group consisting of the following compounds (v-1) and (v-2):
(v-1) at least one Y compound selected from the group consisting of compounds of elements defined as Y in formula (I), wherein said Y compound does not have a rutile structure, and
(v-2) at least one Z oxide selected from the group consisting of oxides of elements defined as Z in formula (I), wherein said Z oxide has a rutile structure; and optionally
(vi) at least one Q compound selected from the group consisting of compounds of elements defined as Q in formula (I), wherein said Q compound does not have a rutile structure,
wherein said Mo compound, said V compound, said Nb compound, said X compound, said Y compound, said Z oxide and said Q compound are, respectively, used in amounts such that the atomic ratios of the Mo, V, Nb, X, Y, Z and Q in the catalyst obtained satisfy the atomic ratio requirements defined for formula (I).

* * * * *